(12) United States Patent
Datla et al.

(10) Patent No.: US 7,393,997 B2
(45) Date of Patent: Jul. 1, 2008

(54) METHODS FOR MODIFICATION OF PLANT INFLORESCENCE ARCHITECTURE

(76) Inventors: Raju Datla, 422 Tennant Way, Saskatoon, Saskatchewan (CA) S7H 5C4; Tim Dumonceaux, 2236 Ewart Avenue, Saskatoon, Saskatchewan (CA) S7J 1Y2; Prakash Venglat, 1901 Dufferin Avenue, Saskatoon, Saskatchewan (CA) S7J 1B6; Vivijan Babic, 1108 6th Street, Saskatoon, Saskatchewan (CA) S7H 1E3; Wilf Keller, 234 Emmerline Road, Saskatoon, Saskatchewan (CA) S7J 5B6; Gopalan Selvaraj, 540 Nesslin Crescent, Saskatoon, Saskatchewan (CA) S7J 4V5

( * ) Notice: Subject to any disclaimer, the term of this patent is extended or adjusted under 35 U.S.C. 154(b) by 300 days.

(21) Appl. No.: 10/471,756

(22) PCT Filed: Mar. 28, 2002

(86) PCT No.: PCT/CA02/00434

§ 371 (c)(1),
(2), (4) Date: Mar. 26, 2004

(87) PCT Pub. No.: WO02/079463

PCT Pub. Date: Oct. 10, 2002

(65) Prior Publication Data

US 2005/0066395 A1 Mar. 24, 2005

Related U.S. Application Data

(60) Provisional application No. 60/281,901, filed on Mar. 29, 2001.

(51) Int. Cl.
*C12N 15/29* (2006.01)
*C12N 15/82* (2006.01)
*C12N 5/04* (2006.01)
*A01H 5/00* (2006.01)

(52) U.S. Cl. ............... 800/278; 800/298; 800/287; 800/290; 800/306; 435/410; 435/419; 536/23.6

(58) Field of Classification Search ............ 800/278, 800/298, 290, 287, 306; 536/23.1; 435/468
See application file for complete search history.

(56) References Cited

U.S. PATENT DOCUMENTS 6,060,644 A 5/2000 Hansen et al. ............ 800/281

6,509,191 B2 * 1/2003 Liu et al. ............ 435/419

OTHER PUBLICATIONS

Lincoln et al (1994, The Plant Cell 6:1859-1876).*
Bowie et al, Science 247:1306-1310, 1990.*
McConnell et al, Nature 411 (6838):709-713, 2001.*
Benfey et al (1990, Science 250:959-966).*
Benfey et al (1989, EMBO J, 8(8):2195-2202).*
Kano-Murakami et al (1993, FEBS 334:365-368).*
2006, Merriam-Webster Online Dictionary.*
Douglas Scott J et al: "KNAT1 and *erecta* regulate inflorescence architecture in *Arabidopsis*." Plant Cell, vol. 14, No. 3, Mar. 2002, pp. 547-558, XP002217925, Mar. 2002, ISSN: 1040-4651.
Koornneef M et al: "Linkage Map of *Arabidopsis-thaliana*", Journal of Heredity, vol. 74, No. 4, 1983, pp. 265-272, XP002217923, ISSN: 0022-1503, cited in the application.
Lincoln C et al: "A knotted1-like homeobaox gene in *Arabidopsis* is expressed in the vegetative meristem and dramatically alters leaf morphology when overexpressed in transgenic plants", Plant Cell, American Society of Plant Physiologists, Rockville, MD, US, Dec. 1994, pp. 1859-1876, XP002075916, ISSN: 1040-4651, cited in the application.
Mayer K et al: "Sequence and analysis of chromosome 4 of the plant *Arabidopsis thaliana* ", Nature, MacMillan Journals Ltd. London, GB, vol. 402, No. 6763, Dec. 16, 1999, pp. 769-777, XP002159526, ISSN: 0028-0836.
Rhee S Y et al: "Genome maps 9. *Arabidopsis thaliana*. Wall chart.", Science. United States Oct. 23, 1998, vol. 282, No. 5389, Oct. 23, 1998, pp. 663-667, XP002217924, ISSN: 0036-8075.
Riggs Daniel et al: "Christmas tree: A *brevipedicellus*-like mutant of *Arabidopsis*", Plant Physiology, American Society of Plant Physiologists, Rockville, MD, US, vol. 114, No. 3 Suppl, 1997, pp. 309, XP002188217, ISSN: 0032-0889.

* cited by examiner

*Primary Examiner*—Stuart F. Baum
(74) *Attorney, Agent, or Firm*—Michael R. Williams; Adrian D. Battison; Ryan W. Dupuis

(57) ABSTRACT

The present invention relates to methods for the use of the *Arabidopsis* "BREVIPEDICELLUS" (BP) gene for alteration of plant architecture, in particular alteration of the morphology of the inflorescence of a flowering plant. The methods of the present invention provide a means to alter the development of the peduncle, notably the inflorescence branches, and the pedicels that subtend the individual flowers as well as aspects of flower structure such as the style, and subsequent seed pods, of a flowering plant. The invention also relates to methods to identify and isolate polynucleotides encoding genes with BP-related functions from other plant species and methods for utilizing said polynucleotides to alter the inflorescence of said plant species. Furthermore, the invention encompasses transgenic plants generated by the methods disclosed, and nucleotide sequences for use in generating the transgenic plants.

15 Claims, 9 Drawing Sheets

Figure 1:
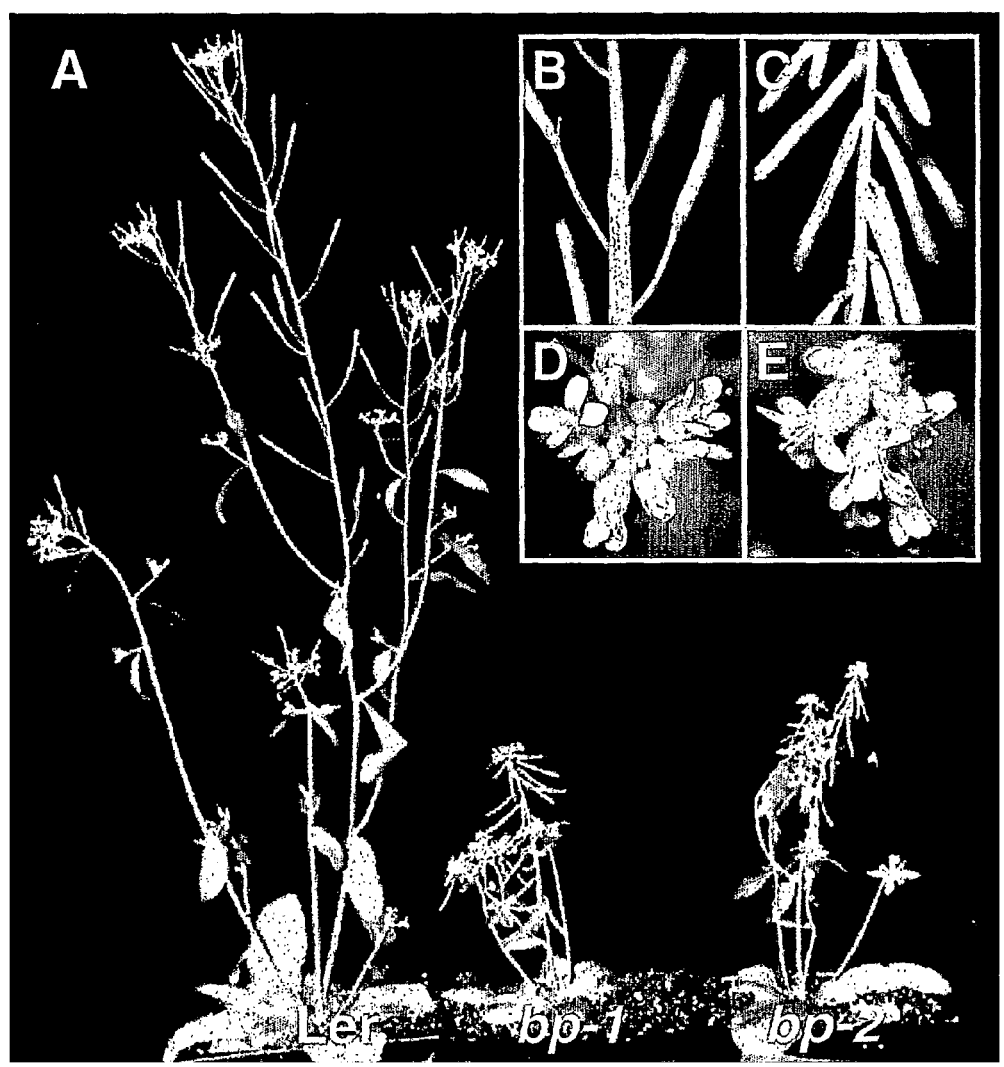

```
                                                                    t bp-2/Ler/RLD
atggaagaataccagcatgacaacagcaccactcctcaaagagtaagtttcttgtactct     60
 M  E  E  Y  Q  H  D  N  S  T  T  P  Q  R  V  S  F  L  Y  S      20
                        S bp-2/Ler/RLD
ccaatctcttcttccaacaaaaacgatacaagtgataccaacaacaacaacaacaacaat    120
 P  I  S  S  S  N  K  N  D  N  T  S  D  T  N  N  N  N  N  N      40
aataatagtagcaattatggtcctggttacaataatactaacaacaatcatcaccac       180
 N  N  S  S  N  Y  G  P  G  Y  N  N  T  N  N  N  N  H  H  H      60
                                                      t Ler
caacacatgttgttccacatatgagctctctcccctcaaacaaccgagaattgcttc       240
 Q  H  M  L  F  P  H  M  S  S  L  L  P  Q  T  T  E  N  C  F      80
    c bp-2              (aac)Ler/RLD---- bp-2      D Ler
cgatctgatcatgatcaaccaacaacaaccatctgttaaatctgaagctagc            300
 R  S  D  H  D  Q  P  N  N  N  N  P  S  V  K  S  E  A  S        100
                         (N)Ler/RLD-  - bp-2
tcctcaagaatcaatcattactgttaatgagagccatccacaatactcaagaagct        360
 S  S  R  I  N  H  Y  S  M  L  M  R  A  I  H  N  T  Q  E  A     120
(aac)Ler/RLD                        t bp-2
aacaacaacaacaatgacaacgtaagcgatgtgttgaagcgatgaaggccatgaaggccatgaaatcattgct    420
 N  N  N  N  N  D  N  V  S  D  V  E  A  M  K  A  K  I  I  A     140
(N)Ler/RLD
catcctcactactcctacaagcttacttggactgccaaaagattggagctcca           480
 H  P  H  Y  S  T  L  L  Q  A  Y  L  D  C  Q  K  I  G  A  P     160
    c bp-2                                          t bp-2
cctgatgtggttgatagaattacggcggcacggcaaggcacggcaagacttgaggctgacaacagcgg        540
 P  D  V  V  D  R  I  T  A  A  R  Q  D  F  E  A  R  Q  Q  R  •   180
                                                      bp-2
```

FIG. 7

SEQUENCE LISTING

<160> NUMBER OF SEQ ID NOS: 24

<210> SEQ ID NO 1
<211> LENGTH: 29
<212> TYPE: DNA
<213> ORGANISM: Artificial sequence
<220> FEATURE:

-continued

```
<223> OTHER INFORMATION: 954 DNA SEQ - PCR primer

<400> SEQUENCE: 1
cgggatccat ggaagaatac cagcatgac                                        29

<210> SEQ ID NO 2
<211> LENGTH: 34
<212> TYPE: DNA
<213> ORGANISM: Artificial sequence
<220> FEATURE:
<223> OTHER INFORMATION: 955 DNA SEQ - PCR primer

<400> SEQUENCE: 2
cgggatccgg tacctggatg tcttatggac cgag                                  34

<210> SEQ ID NO 3
<211> LENGTH: 19
<212> TYPE: DNA
<213> ORGANISM: Artificial sequence
<220> FEATURE:
<223> OTHER INFORMATION: DNA SEQ gapC-UP - PCR primer

<400> SEQUENCE: 3
accactaact gccttgctc                                                   19

<210> SEQ ID NO 4
<211> LENGTH: 22
<212> TYPE: DNA
<213> ORGANISM: Artificial sequence
<220> FEATURE:
<223> OTHER INFORMATION: DNA SEQ gapC-DN

<400> SEQUENCE: 4
caatttcaca aacttgtcgc tc                                               22

<210> SEQ ID NO 5
<211> LENGTH: 1227
<212> TYPE: DNA
<213> ORGANISM: Arabidopsis sp.

<400> SEQUENCE: 5
cgggatccat ggaagaatac cagcatgaca acagcaccac tcctcaaaga gtaagttttct     60 tgtactctcc aatctcttct tccaacaaaa acgataacac aagtgatacc aacaacaaca    120
acaacaataa taatagtagc aattatggtc ctggttacaa taatactaac aacaacaatc    180
atcaccacca acacatgttg tttccacata tgagctctct tctccctcaa acaaccgaga    240
attgcttccg atctgatcat gatcaaccca acaacaacaa caacccatct gttaaatctg    300
aagctagctc ctcaagaatc aatcattact ccatgttaat gagagccatc cacaatactc    360
aagaagctaa caacaacaac aatgacaacg taagcgatgt tgaagccatg aaggctaaaa    420
tcattgctca tcctcactac tctaccctcc tacaagctta cttggactgc caaaagattg    480
gagctccacc tgatgtggtt gatagaatta cggcggcacg gcaagacttt gaggctcgac    540
aacagcggtc aacaccgtct gtctctgcct cctctagaga cccggagtta gatcaattca    600
tggaagcata ctgtgacatg ttggttaaat atcgtgagga gctaacaagg cccattcagg    660
aagcaatgga gtttatacgt cgtattgaat ctcagcttag catgttgtgt cagagtccca    720
ttcacatcct caacaatcct gatgggaaga gtgacaatat gggatcatca gacgaagaac    780
aagagaataa cagcggaggg gaaacagaat accggaaat agacccgagg ccgaagatc     840 gggaactcaa gaaccatttg ctgaagaagt atagtggata cttaagcagt ttgaagcaag    900
```

```
aactatccaa gaagaaaaag aaaggtaaac ttcctaaaga agcacggcag aagcttctca    960
cgtggtggga gttgcattac aagtggccat atccttctga gtcagagaag gtagcgttgg   1020
cggaatcaac ggggttagat cagaaacaaa tcaacaattg gttcataaac caaagaaagc   1080
gtcactggaa accatctgaa gacatgcagt tcatggtgat ggatggtctg cagcacccgc   1140
accacgcagc tctgtacatg gatggtcatt acatgggtga tggaccttat cgtctcggtc   1200
cataagacat ccaggtaccg gatcccg                                       1227

<210> SEQ ID NO 6
<211> LENGTH: 1221
<212> TYPE: DNA
<213> ORGANISM: Arabidopsis sp.

<400> SEQUENCE: 6
cgggatccat ggaagaatac cagcatgaca cagctccac tcctcaaaga gtaagtttct     60
tgtactctcc aatctcttct tccaacaaaa acgataacac aagtgatacc aacaacaaca   120
acaacaataa taatagtagc aattatggtc ctggttacaa taatactaac aacaacaatc   180
atcaccacca acacatgttg tttccacata tgagctctct tctccctcaa caaccgaga   240 attgcttccg atccgatcat gatcaaccca caacaaccc atctgttaaa tctgaagcta   300
gctcctcaag aatcaatcat tactccatgt taatgagagc catccacaat actcaagaag   360
ctaacaacaa caacaatgat aacgtaagcg atgttgaagc catgaaggct aaaatcattg   420
ctcatcctca ctactctacc ctcctacaag cttacttgga ctgccaaaag attggagctc   480
cacctgacgt ggttgataga attacggcgg cacggcaaga ctttgaggct cgacaatagc   540
ggtcaacacc gtctgtctct gcctcctcta gagacccgga gttagatcaa ttcatggaag   600
catactgtga catgttggtt aaatatcgtg aggagctaac aaggcccatt caggaagcaa   660
tggagtttat acgtcgtatt gaatctcagc ttagcatgtt gtgtcagagt cccattcaca   720
tcctcaacaa tcctgatggg aagagtgaca atatgggatc atcagacgaa gaacaagaga   780
ataacagcgg aggggaaaca gaattaccgg aaatagaccc gagggccgaa gatcgggaac   840
tcaagaacca tttgctgaag aagtatagtg gatacttaag cagtttgaag caagaactat   900
ccaagaagaa aaagaaaggt aaacttccta agaagcacg gcagaagctt ctcacgtggt   960
gggagttgca ttacaagtgg ccatatcctt ctgagtcaga gaaggtagcg ttggcggaat  1020
caacggggtt agatcagaaa caaatcaaca attggttcat aaaccaaaga aagcgtcact  1080
ggaaaccatc tgaagacatg cagttcatgg tgatggatgg tctgcagcac ccgcaccacg  1140
cagctctgta catggatggt cattacatgg gtgatggacc ttatcgtctc ggtccataag  1200
acatccaggt accggatccc g                                            1221

<210> SEQ ID NO 7
<211> LENGTH: 176
<212> TYPE: PRT
<213> ORGANISM: Arabidopsis sp.

<400> SEQUENCE: 7

Met Glu Glu Tyr Gln His Asp Asn Ser Ser Thr Pro Gln Arg Val Ser
1               5                  10                  15

Phe Leu Tyr Ser Pro Ile Ser Ser Asn Lys Asn Asp Asn Thr Ser
            20                  25                  30

Asp Thr Asn Asn Asn Asn Asn Asn Asn Ser Ser Asn Tyr Gly Pro
        35                  40                  45
```

```
Gly Tyr Asn Asn Thr Asn Asn Asn His His His Gln His Met Leu
        50                  55                  60

Phe Pro His Met Ser Ser Leu Leu Pro Gln Thr Thr Glu Asn Cys Phe
 65                  70                  75                  80

Arg Ser Asp His Asp Gln Pro Asn Asn Pro Ser Val Lys Ser Glu
                 85                  90                  95

Ala Ser Ser Ser Arg Ile Asn His Tyr Ser Met Leu Met Arg Ala Ile
                100                 105                 110

His Asn Thr Gln Glu Ala Asn Asn Asn Asn Asp Asn Val Ser Asp
            115                 120                 125

Val Glu Ala Met Lys Ala Lys Ile Ile Ala His Pro His Tyr Ser Thr
        130                 135                 140

Leu Leu Gln Ala Tyr Leu Asp Cys Gln Lys Ile Gly Ala Pro Pro Asp
145                 150                 155                 160

Val Val Asp Arg Ile Thr Ala Ala Arg Gln Asp Phe Glu Ala Arg Gln
                165                 170                 175

<210> SEQ ID NO 8
<211> LENGTH: 35
<212> TYPE: DNA
<213> ORGANISM: Artificial sequence
<220> FEATURE:
<223> OTHER INFORMATION: DNA SEQ 951 - PCR primer

<400> SEQUENCE: 8
cccaagctta gatctttcgg tctagtgcag tgatg                          35

<210> SEQ ID NO 9
<211> LENGTH: 26
<212> TYPE: DNA
<213> ORGANISM: Artificial sequence
<220> FEATURE:
<223> OTHER INFORMATION: DNA SEQ 952 - PCR primer

<400> SEQUENCE: 9
ccggatccca gatgagtaaa gatttg                                    26

<210> SEQ ID NO 10
<211> LENGTH: 38
<212> TYPE: DNA
<213> ORGANISM: Artificial sequence
<220> FEATURE:
<223> OTHER INFORMATION: DNA SEQ 956 - PCR primer

<400> SEQUENCE: 10
gaagatctgt cgacgccttg tgcttgattg agactcca                       38

<210> SEQ ID NO 11
<211> LENGTH: 1515
<212> TYPE: DNA
<213> ORGANISM: Brassica napus

<400> SEQUENCE: 11
ggcacgagca cattagtttt ttatattctc tctctctctc tctctttctc tctcaacttt    60
tattcatctg ggtatggaag aatatcaaca tgaaagcaga tccactcctc atagagtaag   120
tttcttgtac tctccaatct cttcttccaa caaaaatgat aacaccacca ccaacaacaa   180
taataccaat tatggttctg ttacaataa  tactaataac aataatcatc aacaacacat   240
gttgttccca catatgagct ctcttcttcc tcaaacgact gagaattgct tccgatccga   300
```

```
tcatgatcag cctaccaacg catctgttaa atcagaagca agctcctcaa gaatcaatca    360
ctactctatg ttgatgaaag ccatccacaa tactcaagaa actaacaaca acaacaatga    420
tacggaatcc atgaaagcta agatcatcgc tcatccccac tactccaccc tcctacacgc    480
ctacttggac tgccagaaga ttggagcacc acctgaggtg gtcgataaaa ttacggcggc    540
aagacaagag ttcgaggcga ggcagcagcg ccaacagcg tccgtaactg cgctgtctag    600
agacccggaa ttggatcaat tcatggaagc atactgtgat atgctggtta aatatcgaga    660
ggagctaaca cggcccattg aagaagcaat ggagtatata cgtcgtattg aatctcaaat    720
tagcatgttg tgtcagggtc ccattcacat cctcaacaat cctgatggga aaagtgaagg    780
aatagaatca tcagacgaag agcaagataa taacaacagt ggaggggaag cagaattacc    840
ggaaatagac ccgagggcgg aagatcggga actcaagaat cacttgctga agaagtacag    900
tggatacttg agcagtctaa agcaagaact gtccaagaaa aaaagaaag gtaaacttcc    960 caaagaagca aggcagaagc ttctcacgtg gtgggaattg cattacaagt ggccgtatcc    1020
ttctgaatca gagaaggtgg cgttggcgga atcaacgggg ttagatcaga aacagatcaa    1080
caattggttc ataaaccaaa gaaaacgtca ctggaaaccg tccgaggaca tgcagttcat    1140
ggtgatggat ggtctacagc acccgcacca cgcagctcta tacatggatg gtcattacat    1200
gggcgatggt ccttatcgtc ttggaccata agagaccaca tgcagatatc cagaagggtt    1260
agccatataa taacaaccct ttgttgcctc tctcgtttac agttcatgat ttcaactttc    1320
cttcacaagt ttgctaccta tagctttatt ttcttacccg tatttaatgt cttatatcgt    1380
tcaaggggtt tgagacttcc tagtcatttt cacttttttat tttgtatttt tcataatgtt    1440
ttatttataa tatgtgttct aataatgtgt gaaaagagat gtttttatga attttaaaaa    1500
aaaaaaaaaa aaaaa                                                   1515

<210> SEQ ID NO 12
<211> LENGTH: 29
<212> TYPE: DNA
<213> ORGANISM: Artificial sequence
<220> FEATURE:
<223> OTHER INFORMATION: PCR primer

<400> SEQUENCE: 12
cgggatccat ggaagaatat caacatgaa                                       29

<210> SEQ ID NO 13
<211> LENGTH: 31
<212> TYPE: DNA
<213> ORGANISM: Artificial sequence
<220> FEATURE:
<223> OTHER INFORMATION: PCR primer

<400> SEQUENCE: 13
cgggatccgg taccttatgg tccaagacga t                                    31

<210> SEQ ID NO 14
<211> LENGTH: 1186
<212> TYPE: DNA
<213> ORGANISM: Brassica rapa

<400> SEQUENCE: 14
cgggatccat ggaagaatat caacatgaaa gcagatccac tcctcataga gtaagtttct    60
tgtactctcc aatctcttct tccaacaaaa atgataacac caccaccaac aacaataata    120
ccaattatgg ttctggttac aataatacta ataacaataa tcatcaacaa cacatgttgt    180
```

```
tcccacatat gagctctctt cttcctcaaa cgactgagaa ttgcttccga tccgatcatg      240
atcagccaac caacgcatct gttaaatcag aagcaagctc ctcaagaatc aatcactact      300
ctatgttgat gaaagccatc cacaatactc aagaagctaa caacaacaac aacaacaayg      360
atatggaatc catgaaagct aagatcatcg ctcatcctca ctactccacc ctcctacacg      420
cctacttgga ctgccagaag attggagcac cacctgaagt ggttgataaa attacggcgg      480
caagacaaga attcgaggcg aggcagcagc ggccaacagc gtccgtaact gcgctgtcta      540
gagaccccga attggatcaa ttcatggaag catactgtga tatgctggtt aaatatcgag      600
aggagctaac acgcccatt  gaagaagcaa tggagtatat acgtcgtatt gaatctcaga      660
ttagcatgtt gtgtcagggt cccattcaca tcctcaacaa tcctgatggg aaaagtgaag      720
gaatggaatc atcagacgaa gagcaagata ataacaacag tggaggggaa gcagaattac      780
cggaaataga cccgagggcg aagatcggg  aactcaagaa tcacttgctg aagaaataca      840
gtggatactt gagcagtcta aagcaagaac tgtccaagaa aaaaaagaaa ggtaaacttc      900
ccaaagaagc aaggcagaag cttctcacgt ggtgggaatt gcattacaag tggccgtatc      960
cttctgaatc agagaaggtg gcgttggcgg aatcaacggg gttagatcag aaacagatca     1020
acaattggtt cataaaccaa agaaaacgtc actggaaacc gtccgargac atgcagttca     1080
tggtgatgga tggtctacag cacccgcacc acgcagctct atacatggat ggtcattaca     1140
tgggcgatgg cccttatcgt cttggaccat aaggtaccgg atcccg                    1186
```

<210> SEQ ID NO 15
<211> LENGTH: 1180
<212> TYPE: DNA
<213> ORGANISM: Brassica oleracea
<220> FEATURE:
<221> NAME/KEY: misc_feature
<222> LOCATION: (1078)..(1078)
<223> OTHER INFORMATION: n = a, c, g, or t

<400> SEQUENCE: 15

```
cgggatccat ggaagaatat caacatgaaa gcagatccac tcctcataga gtaagtttct       60
tgtactctcc aatctcttct tccaacaaaa atgataacac caccaccaac aacaataata      120
ccaattatgg ttctggttac aataatacta ataacaataa tcatcaacaa cacatgttgt      180
tcccacatat gagctctctt cttcctcaaa cgactgagaa ttgcttccga tccgatcatg      240
atcagcctac caacgcatct gttaaatcag aagcaagctc ctcaagaatc aatcactact      300
ctatgttgat gaaagccatc cacaatactc aagaaactaa caacaacaac aatgatacgg      360
aatccatgaa agctaagatc atcgctcatc cccactactc caccctccta cacgcctact      420
tggactgcca gaagattgga gcaccacctg aggtggtcga taaaattacg gcggcaagac      480
aagagttcga ggcgaggcag cagcggccaa cagcgtccgt aactgcgctg tctagagacc      540
cggaattgga tcaattcatg gaagcatact gtgatatgct ggttaaatat cgagaggagc      600
taacacggcc cattgaagaa gcaatggagt atatacgtcg tattgaatct caaattagca      660
tgttgtgtca gggtcccatt cacatcctca acaatcctga tgggaaaagt gaaggaatag      720
aatcatcaga cgaagagcaa gataataaca acagtggagg ggaagcagaa ttaccggaaa      780
tagacccgag ggcggaagat cgggaactca agaatcactt gctgaagaag tacagtggat      840
acttgagcag tctaaagcaa gaactgtcca agaaaaaaaa gaaaggtaaa cttcccaaag      900
aagcaaggca gaagcttctc acgtggtggg aattgcatta caagtggccg tatccttctg      960
```

```
aatcagagaa ggtggcgttg gcggaatcaa cggggttaga tcaaaaacag atcaacaatt    1020
ggttcataaa ccaaagaaaa cgtcactgga aaccgtccga ggacatgcag ttcatggnga    1080
tggatggtct acagcacccg caccacgcag ctctatacat ggatggtcat tacatgggcg    1140
atggtcctta tcgtcttgga ccataaggta ccggatcccg                          1180

<210> SEQ ID NO 16
<211> LENGTH: 20
<212> TYPE: DNA
<213> ORGANISM: Artificial sequence
<220> FEATURE:
<223> OTHER INFORMATION: PCR primer

<400> SEQUENCE: 16
ataacaccac caccaacaac                                                  20

<210> SEQ ID NO 17
<211> LENGTH: 20
<212> TYPE: DNA
<213> ORGANISM: Artificial sequence
<220> FEATURE:
<223> OTHER INFORMATION: PCR primer

<400> SEQUENCE: 17
actaggaagt ctcaaacccc                                                  20

<210> SEQ ID NO 18
<211> LENGTH: 21
<212> TYPE: DNA
<213> ORGANISM: Artificial sequence
<220> FEATURE:
<223> OTHER INFORMATION: PCR primer

<400> SEQUENCE: 18
tcaacatgaa agcagatcca c                                                21

<210> SEQ ID NO 19
<211> LENGTH: 20
<212> TYPE: DNA
<213> ORGANISM: Artificial sequence
<220> FEATURE:
<223> OTHER INFORMATION: PCR primer

<400> SEQUENCE: 19
aacgagagag gcaacaaaag                                                  20

<210> SEQ ID NO 20
<211> LENGTH: 3750
<212> TYPE: DNA
<213> ORGANISM: Brassica napus

<400> SEQUENCE: 20
ataacaccac caccaacaac aataatacca attatggttc tggttacaat aatactaata      60
acaataatca tcaacaacac atgttgttcc cacatatgag ctctcttctt cctcaaacga     120
ctgagaattg cttccgatcc gatcatgatc agccaaccaa cgcatctgtt aaatcagaag     180
caagctcctc aagaatcaat cactactcta tgttgatgaa agccatccac aatactcaag     240
aagctaacaa caacaacaac aacaatgata tggaatccat gaaagctaag atcatcgctc     300
atccgcacta ctccaccctc ctacacgcct acttggactg ccagaaggtt atatagattt     360
agcactggat ttcgttttat ttttgttgta gtaatatata aaataccact cttgtttgtt     420
taaattaacg agatgatatg cgtaaatatg ttcacgggtt gcatatacag attggagcac     480
```

```
cacctgaagt ggttgataaa attacggcgg caacacaaga gttcgaggcg aggcagcagc    540
ggccaacagc atccgtaact gcgctgtcta gagaccccga attggatcaa ttcatggtaa    600
attaattatc aaactgaatt atagtgggtc gtttcttcaa gtgtatatgt taagtcttta    660
tttttgtttg tatcgtaaat tttatcaaca ggaagcatac tgtgatatgc tggttaaata    720
tcgagaggag ctaacacggc ccattgaaga agcaatggag tatatacgtc gtattgaatc    780
tcagattagc atgttgtgtc agggtcccat tcacatcctc aacaatcctg gtaaatgtca    840
taaaactcac aaatacatat acatgcatat acccacatgt aaccattgaa tgtagaaaag    900
aaaatataat gccaaggtag ggctcatgat gaatttcaag agcaacattg gcgcgtattt    960
ctttggttcc cgggaaagtt ttgtaccaat tagattatga taaggcgacc aaaaaataat   1020
tatgattata tttggttaaa attttttcatc taaacattca agtgttaatt aagatcataa   1080
aatataatag ttaatatgat agaaattcgt aggctgcaga cagatgtgca catttgctct   1140
tgttttccct attgtagaat ccatccaaag agggtggggc ttttttttggt ttcttacttt   1200 taacccggcc caaagtacta ctgtcacaaa cacttttttgt tgttcactat gaaaaaaat    1260 acaaataggt attctcaatt ccagtatgca aaatgtttca aattttcata aaaaagtcag   1320
tacgactaaa ttgctcgtga attatgaatc aaaatataag actgatgaaa agctaaaatt   1380
tgaaacagat gggaaaagtg aaggaatgga atcatcagac gaagagcaag ataataacaa   1440
cagtggaggg gaagcagaaa ttaccggaaa tagacccgga gggcggaaga tcgggaactc   1500
aagaatcact tgctgaagaa gtacagtgga tacttgagca gtctaaagca agaactgtcc   1560
aagaaaaaaa agaaaggtaa acttcccaaa gaagcaaggc agaagcttct cacgtggtgg   1620
gaattgcatt acaagtggcc gtatccttct gtacgtataa ttttactctc atctctctat   1680
gctttcagtc ttttaaaata tacactctat ataaatacta gaaccagtct tttggaaaac   1740
aatgtagatg ctgggaatct ccaatttgcc ctgattttct ctaaagggcc ttccttaggc   1800
cgattaggct ctttgcaggg atcatttgta gatgctaggc tctttgcaga gataaatttgt   1860 gttcaaacct ttatgcgttt ccatatttca taacatatgt atatatacat atatcaaaca   1920 cgttttatc tatagttatc taaattttga ataatttttg aagtttaagt ccgtggatct    1980
attgttatag tttatcagct tcaggaaata aaacaaataa aaccgaatgt ggtgatggcg   2040
aaggtcttta atattgggta tacatattta ccacaaaaaa aatgatatat tatatagaat   2100
ggctgtttgt tgttaaaaaaa tcctggtatt tttttttggta aatatgatac catttccaat   2160
gaacaccaaa aatgatacca tcccaccaaa tttgttgtaa tgtaaaaagt attacaccaa   2220
attaacaata ttcattacac caaatattaa aataatatat tttattattt tttatttaat   2280
aatagataga ttagttttttt acttagttat aacttatagt taaaatgagt atatcataat   2340
atcttgtatt tttaatccat atttttacat tactaaaaca ttaaactatt attttatttt   2400
ataatttaat taatagtata taattaaatg agtattataa attatattaa atggtaacaa   2460
aataaaaatg atcttcattt taaatgcaaa agtttttaat ttttacaaat attttaaata   2520
aaataaataa taaagtatac acattmacta aaagaaaaat agcttatata aaaataaaat   2580
taccaaatat taatatatat atatatatat atataaacta aatgtgatac atatatataa   2640
ttagtcaatt ataaacaatt aatgtattaa attactaaaa ctaaaagtt gataatataa     2700 aatattattt tggtgtagaa tttggtgtga tggttggaca tgaaaataa agtttaacmc     2760 ttaaacmccm mtyctggtgt aatttcarca ctaatttttag tgttatggtt ggagataccc   2820
```

-continued

```
taacagaacc atgcttcgtg ctttgaaaaa aaaatcagtc gtctaaagct acaataaaaa    2880
aattggaggg aaatattttg tttcaaatta ggttatgtat ttacacagat atttgtttgg    2940
attcttgtct gagaagtgca tggcattaca ttttgtgtta caaaagaagt tgaatgatct    3000
gagtatcata tttattgaaa gcgtgttggt atatgtgtgt tgctaaaaag ttctataaga    3060
aaattggata aatttgcttt aaaatttcca tagtatatca ctattttgta tgttcggaaa    3120
ccttgatatg tatactttc ccttataacg agggccttaa tattctttag tcatctagat     3180
tgttcgaagc agcagactgt aatttataac ttcgtctgac tatcatctac cttttttata    3240
gaacatacct tttcttttat tgaaactaat atcgtctagc ttttgtgatt aaatctaccg    3300
tttttaaaca atgaacaata ctaaaaaagt gatgatatgg atatggttct gatttgtgtt    3360
gtgtggcagg agtcagagaa ggtggcgttg gcggaatcca acggggttag atcagaaaca    3420
gatcaacaat tggttcataa accaagaaaa acgtcactgg aaaccgtccg aagacatgca    3480
gttcatggtg atgatggtc tacagcaccc gcaccacgca gctctataca tggatggtca    3540
ttacatgggc gatggtcctt atcgtcttgg accataagag accgcatgca gatatccaga    3600
agggttagcc atataataac aacctttgt tgcctctctc gtttacagtt catgatttca     3660
actttccttc acaagtttgc tacctatagc tttatttct tacccgtatt taatgtctta     3720
tatcgttcaa ggggtttgag acttcctagt                                     3750
```

<210> SEQ ID NO 21
<211> LENGTH: 30
<212> TYPE: DNA
<213> ORGANISM: Artificial sequence
<220> FEATURE:
<223> OTHER INFORMATION: PCR primer

<400> SEQUENCE: 21

```
catgatcgga tcggaagcaa ttctcagtcg                                       30
```

<210> SEQ ID NO 22
<211> LENGTH: 30
<212> TYPE: DNA
<213> ORGANISM: Artificial sequence
<220> FEATURE:
<223> OTHER INFORMATION: PCR primer

<400> SEQUENCE: 22

```
aaaagttgag agagaaagag agagagagag                                       30
```

<210> SEQ ID NO 23
<211> LENGTH: 840
<212> TYPE: DNA
<213> ORGANISM: Brassica napus

<400> SEQUENCE: 23

```
aaaaaatgct tacaaatatc tgcacatcaa ccaatctgtt acataaatag atcttcttgt      60
gggggtaggg ttaacaaata ttttcctctt tttcttttct caaaaatgta tcggtactga     120
tatagccgcg gagacctggt tcattaaaac attggcggta catcttaata atcaaaacat     180
tgacggcaca tcttaatcct agagtttaac cacattatat atcatagagt aacaaactta     240 gttttgtgacc caaagaaga aaaaaaactt ccaattttct agtacagaat aagcctacga     300
gagggaaaca gaagagaaag gaggaaagaa gggaagcctt tgccttatct cttgtccatt     360
ctctcttacc tttattttta attttcaaat atttattatt gccaccaaag caaacgacgt     420
cttgtcaatc cactcaaccc acccaacttc ttaattattg ttaacacatc tctcctcttt     480
```

-continued

```
ctctctcatc tttttataat ttcttctctt ccatgtcact ttttgacgaa ttctatttac    540
ttagttcgtt ttttcttcct caaaatatct cgttttcaat ttatttgttt tgttgggtgc    600
aacttcacct cacaatttt tttatgaagc acctttctga ttcgtagata tgagtcgtct     660
agtcatgtgg atttgatttg gttaaagtct aacatcgacc tttgattgaa ataaggacaa    720
aagaaagaat acatacatcc ccttcatttt gcacccatcc ctttattttc tagggtttta    780
tttttatcac attagttttt tatattctct ctctctctct ctctttctct ctcaactttt   840

<210> SEQ ID NO 24
<211> LENGTH: 950
<212> TYPE: DNA
<213> ORGANISM: Brassica napus

<400> SEQUENCE: 24
aaatctttat cttctctgtt tcttgtgcaa tcttctatcc gaaaacgagt acaatataat     60
ctctctccac cgatgtaata cgaatatcaa atcagaaatt aatcatttga tcatattctc    120
aaaacatcta aatttatttt acaaattgct tacaaatatc tgcacatcaa ccaatctgtt    180
acataaatag atcttcttgt aggggtaagg ttaacaaata ttttttctt tttcttttct    240 ccaaaatgta tcggtactga tatagccgcg gagacctggt tcatcaaaac attgacggta    300
catcttaatt cgagagttta accaaattat atcatagagt aacaaactta gtttttgacc   360
caaaataaga gaaaaaactt tcaattttct aatacggaat aagctatgag agggagacag    420
aagagaaagt aggaagaag ggaagccttt gccttatctc ttgtccattc tctcttacct     480
ttattttaat tttcaaatat ttattattgc caccaaagca aacgacgtct tgtcaatcca    540
ctcaacccac ccaacttctt aattattgtt aacacatctc tcctctttct ctctcatctt   600
tttataattt cttctcttcc atgtcacttt ttgacgaatt ctatttactt agttcgtttt    660
ttcttcctca aaatatctcg ttttcaattt atttgttttg ttgggtgcaa cttcacctca    720 caatttttt tatgaagcac ctttctgatt cgtagatatg agtcgtctag tcatgtggat     780
ttgatttggt taaagtctaa catcgacctt tgattgaaat aagaacaaaa gaaagaatac    840
atacatcccc ttcatttgc acccatccct ttattttcta gggttttatt tttatcacat    900 tagttttta tattctctct ctctctctct ctctttctct ctcaactttt                 950
```

METHODS FOR MODIFICATION OF PLANT INFLORESCENCE ARCHITECTURE

This application is the National Stage of International Application No. PCT/CA02/00434, filed Mar. 28, 2002 which claims the benefit under 35 U.S.C. 119(e) of U.S. provisional application Ser. No. 60/281,901, now abandoned, filed Mar. 29, 2001.

FIELD OF THE INVENTION

The present invention relates to methods for altering plant architecture, and in particular the morphology of the inflorescence of a flowering plant, involving the use of the *Arabidopsis* "BREVIPEDICELLUS" (BP) gene and homologues thereof.

BACKGROUND OF THE INVENTION

Plant architecture plays a very important role in overall crop performance. The characteristics of the inflorescence, flower, silique/fruit, and stem internodes have broad agronomic implications in the overall productivity of any crop plant. Compact architecture can contribute to productivity. For example, flowering stalks or inflorescences that are compact in nature and do not shade lower photosynthetic tissue can allow for greater productivity. Similarly, a flowering stalk or inflorescence that is spread out may allow for more photosynthesis to take place during seed development within the flowering stalk. Thus, different inflorescence architectures may be desired for different crops.

Since most crop varieties have been derived directly or indirectly through breeding from wild species, productivity of crops may be affected by characteristics that are evolutionarily beneficial to wild species but impair performance in an agricultural setting. For example, well spread-out flowers and siliques with long pedicels on the inflorescence (along with genes controlling seed dispersal mechanisms such as shattering) may be evolutionarily beneficial to wild species, while in a crop setting this confers significant disadvantages in terms of overall productivity as measured by harvested seed.

An example of this is canola species, in which the shoot architecture, especially involving inflorescence and siliques, is not ideal for optimal productivity and recovery of seed. Though there have been concerted efforts to produce crop plants with ideal architecture, it has not been achieved in many crop species.

It widely known that the growth and developmental programs of a plant species control pedicel development and determine its length, attachment angle of the flowers and seed pods, and contribute significantly towards the overall architecture of the flower and/or inflorescence. Despite significant advances in the understanding of flower development, very little is known about the genetic and molecular control of pedicel development.

Plant architecture or morphology is a major determining factor in plant productivity under agricultural settings. Plant varieties that have well-defined morphology of a uniform nature and pattern are preferred since they are amenable to mechanical cultivation. In particular, plant species that produce seed are selected for the uniformity of the placement of seed forming structures (typically seed pods or cobs) to allow efficient mechanical harvesting of seed. Plant varieties are also selected on the basis of other seed forming characteristics, such as strong pods to ensure no seed is lost or dispersed prior to harvesting, or compact nature of the raceme of the plant that contains the seedpods. Not all plants have these ideal characteristics. Thus, there is a strong interest in modifying the placement of seed pods and overall physical characteristics, of many seed plants to produce plants with desirable plant architecture and overall morphology. Compact plants, with clustered seed pods can provide many benefits for mechanical production of the crop, as well as lead to increased productivity. Accordingly, control of plant form and plant architecture is a desirable goal for the industry.

The building blocks of the plant architecture (body plan) are composed of reiterative units referred to as phytomers and these are elaborated during different phases of development (Sussex, I. M. & Kerk, N. M. (2001) Curr. Opin. Plant Biol. 4, 33-37). In *Arabidopsis thaliana*, three types of phytomers have been described (Schultz, E. A. & Hauglm, G. W. (1991) Plant Cell 3, 771-781.). The variations in the number of units and their size among these three main types of phytomers in different plant species contribute to the tremendous architectural diversity observed in flowering plants (Steeves, T. A. & Sussex, I. M. (1989) Patterns in plant development (Cambridge University Press, Cambridge). The activity of the shoot apical meristem (SAM), together with additional meristems, regulates the growth and development of all three types of phytomers (Medford, J. I., Behringer, F. J., Callos, J. D. & Feldmann, K. A. (1992) Plant Cell 4, 631-643 & Simon, R. (2001) Semin. Cell Dev. Biol. 12, 357-362). The SAM contains three major domains defined by cytoplasmic densities and cell division rates: the central zone (CZ), which is responsible for maintaining the pluripotent stem cells; the peripheral zone (PZ), which is involved in the production of lateral organs; and the rib zone (RZ), from which the bulk of the stem is derived (Bowman, J. L. & Eshed, Y. (2000) Trends Plant Sci. 5, 110-115). Recent studies in *Arabidopsis* have shown that several genes, including SHOOTMERISTEMLESS (STM), WUSCHEL and CLAVATA-family receptor kinases and their putative ligands define key functions in the SAM (Brand, U., Hobe, M. & Simon, R. (2001) BioEssays 23, 134-141., Long, J. A., Moan, E. I., Medford, J. I. & Barton, M. K. (1996) Nature 379,66-69, Mayer, K. F., Schoof, H., Haecker, A., Lenhard, A., Jurgens, G. & Laux, T. (1998) Cell 95, 805-815, & Clark, S. E. (2001) Nat. Mol. Cell Biol. 2, 276-284.)

In *Arabidopsis* the inflorescence constitutes the major part of the shoot and thus contributes significantly to the overall shoot architecture. Several genes have been identified in *Arabidopsis* that play key roles in defining the architecture of the shoot/inflorescence. For example, dwarf plants with uniform effects on all phytomers have been associated with altered levels of or defects in the signaling pathways of certain plant hormones (gibberellins or brassinosteriods—Hedden, N. P. & Kamiya, Y. (1997) Annu. Rev. Plant Physiol. Plant Mol. Biol. 48, 431-460, & Richards, D. E., King, K. E., Ait-ali, T. & Harberd, N. P. (2001) Annu. Rev. Plant Physiol. Plant Mol. Biol. 52, 67-88, and references therein). The supershoot (Tantikanjana, T., Yong, J. W., Letham, D. S., Griffith, M., Hussain, M., Ljung, K., Sandberg, G. & Sundaresan, V. (2001) Genes Dev 15, 1577-1588) and altered meristem program (Chaudhury, A. M., Letham, S., Craig, S. & Dennis; E. S. (1993) Plant J. 4, 907-916) mutants display abnormally high levels of cytokinins and produce extensive branching and altered shoot and inflorescence architecture. Auxin polar transport mutants, such as pinformed (Okada, K., Ueda, J., Komaki, M. K., Bell, C. J. & Shimura, Y. (1991) Plant Cell 3, 677-684) and pinoid (Bennett, S. R. M., Alvarez, J., Bossinger, G. & Smyth, D. R. (1995) Plant J. 8, 505-520), form inflorescences that are reduced to pin-like structures that do not produce any lateral organs or meristems. A compact inflorescence is caused by the erecta mutation, which involves a putative receptor kinase (Torii, K. U., Mitsukawa, N., Oosumi, T., Matsuura, Y., Yokoyama, R., Whittier, R. F. & Komeda, Y. (1996) Plant Cell 8, 735-746).

An even stronger effect on inflorescence architecture is conferred in a *Landsberg erecta* (Ler) background by the brevipedicellus (BP) mutation, which is defined by a recessive mutant with compact internodes and short, downward-pointing pedicels (Koornneef, M., Eden, J. v., Hanhart, C. J., Stam, P., Braaksma, F. J. & Feenstra, W. J. (1983) J. Hered. 74, 265-272). Thus, mutants that exhibit altered architecture provide an indication that architecture can be altered, but there is no indication as to the molecular nature of the gene or the mechanisms by which these changes are manifested.

The role of homeobox genes in defining body plan and their evolutionary relationships in animals is well documented (Gehring, W. J., Affolter, M. & Burglin, T. (1994) Annu. Rev. Biochem. 63, 487-526, Kappen, C. (2000) Proc. Natl. Acad. Sci. USA 97, 4481-4486.) More recently, several plant knotted-like homeobox (KNOX) genes have been identified, which form two classes based upon sequence similarities and expression domains (Bharathan, G., Janssen, B., Kellogg, E. & Sinha, N. (1999) Mol. Biol. Evol. 16, 553-563, Reiser, L., Sanchez, B. P. & Hake, S. (2000) Plant Mol. Biol. 42, 151-166, Serikawa, K. A., Martinez-Laborda, A. & Zambryski, P. (1996) Plant Mol. Biol. 32, 673-693.)

In *Arabidopsis*, there are four different class I KNOX genes, STM, KNAT1, KNAT2, and KNAT6 (Long, ibid., Lincoln, C., Long, J., Yamaguchi, J., Serikawa, K. & Hake, S. (1994) Plant Cell 6, 1859-1876 & Semiarti, E., Ueno, Y., Tsukaya, H., Iwakawa, H., Machida, C. & Machida, Y. (2001) Development 128, 1771-1783.) STMis expressed in the SAM, whereas KNAT1 and KNAT2 expression observed in the PZ of the SAM. KNAT1 is also expressed in the cortical cell layers of the peduncle and pedicel. STM, KNAT1 and KNAT2 expression is excluded from the leaf primordia and developing leaves by ASYMMETRICLEAVES 1 and 2 genes (Ori, N., Eshed, Y., Chuck, G., Bowman, J. L. & Hake, S. (2000) Development 127, 5523-5532, & Byrne, M., Barley, R., Curtis, M., Arroyo, J., Dunham, M., Hudson, A. & Martienssen, R. (2000) Nature 408, 967-971). Ectopic expression of KNAT1 and KNAT2 in leaves induces altered symmetry and cell fate, and ectopic meristem/shoot formation from the adaxial surface (Chuck, G., Lincoln, C. & Hake, S. (1996) Plant Cell 8, 1277-1289). To date, loss-of-function mutations in class I KNOX genes are known only for STM and these suggest a critical role in SAM maintenance and function. Significantly, however, no such mutations have previously been described for KNAT1, hampering study of the role of this homeobox gene in plant development.

The future prospects of engineering optimal plant architectures in plant species will depend on the availability of critical morphology controlling genes and knowledge of their functional regulatory properties. For example in canola, the occurrence of an inflorescence and silique with long pedicels may offer some unique challenges and opportunities to develop an ideal architecture for improving productivity.

In summary, there remains a continuing need to develop novel and efficient techniques for modifying the morphology and architecture of plants, such as for example *Brassica* and other plant types, to improve photosynthetic efficiency, overall yield, and harvestability. This need extends to both crops and to horticulturally grown species to improve aesthetic appeal.

SUMMARY OF THE INVENTION

The inventors of the present application have successfully identified the gene responsible for the *brevipedicellus* (bp) mutant in *Arabidopsis*. This mutation is known to give rise to plants having a very compact architecture with shortened siliques pointing downwards. Importantly, the inventors have realized that the successful identification of this gene has important implications on the generation of new crops and other plant species that exhibit advantageously modified morphological features.

In this regard, the inventors have discovered that the bp mutation has several productivity advantages if introduced for example, into canola crop species. In *Arabidopsis*, the mutation results in reduced pedicel length, and siliques pointing downward with compact architecture. These features can improve exposure of upper leaves to sunlight and thereby enhance their photosynthetic efficiency: a well recognized problem in canola, especially during the pod setting and maturation stages. In addition, during harvesting the altered pod dynamics can reduce shattering losses, an important problem facing canola farmers. Further, the downward-pointing flowers may help in reducing disease incidence.

Therefore, the present invention relates, in one embodiment, to nucleic acid sequences derived from *Arabidopsis* encoding a homeobox gene involved in the control of inflorescence architecture, for use in modifying plant inflorescence architecture. In addition, the present invention relates in other embodiments to methods for modifying the morphological phenotype of plants, by introducing the nucleotide sequences encompassed by the present invention into a plant, and expressing the nucleotide sequences as appropriate.

In another embodiment, the present invention relates to nucleic acid sequences derived from *Arabidopsis* encoding a homeobox gene involved in the control of inflorescence architecture, said homeobox gene differing from wild type by at least a change in an amino acid codon to produce a truncated protein.

The invention further relates to the proteins encoded by the nucleic acids encompassed by the invention, and their use.

The present invention also relates to methods for alteration of the expression of a native gene related to inflorescence structure, in particular the reduction in the expression of said gene.

In one aspect of the invention, nucleic acid sequences are provided that encode an altered protein that when expressed confers an altered inflorescence architecture phenotype in *Arabidopsis*, particularly an inflorescence with an altered pedicel, peduncle or style.

In one aspect of the invention, nucleic acid sequences are provided that encode an altered protein that when expressed confers an altered inflorescence architecture phenotype in *Brassica*, particularly an inflorescence with an altered pedicel, peduncle or style.

In another aspect of the present invention methods are described that enable the heterologous expression of the nucleic acid or portions or homologues thereof, described in SEQ ID NO: 5 in a host cell to obtain a plant with an altered inflorescence, more particularly an inflorescence with an altered pedicel, peduncle or style.

In yet another aspect of the present invention, methods are described wherein the nucleic acid sequence or regions thereof as described in SEQ ID NO: 6 and nucleic acids homologous to same are used to alter the architecture of a flowering plant, in particular the inflorescence, more particularly the pedicel, peduncle or style.

In yet another aspect of the present invention, methods are described wherein nucleic acid sequence or regions thereof as described in SEQ ID. NO: 6 and nucleic acids homologous to same are used to alter the architecture of the inflorescence of a plant from the Crucifer (Cruciferae) family, particularly the pedicel, peduncle or style of said plant.

In yet another aspect of the present invention methods are described wherein nucleic acid sequence or regions thereof as described in SEQ ID. NO: 6 and nucleic acids homologous to same are used to alter the architecture of the inflorescence of a plant from the Crucifer (Cruciferae) family, particularly the pedicel of said plant, said plant exhibiting an altered inflorescence, with compact internodes, downward pointing pedicels and siliques that point downward relative to the normal presentation of siliques.

In one embodiment, the present invention provides a method of producing a transgenic plant with a modified inflorescence architecture characterised in that the method comprises the steps of: (a) introducing into a plant cell capable of being transformed and regenerated into a whole plant a construct comprising, in addition to the DNA sequences required for transformation and selection in plants, a nucleotide sequence derived from a KNAT1 gene and encoding at least part of a KNAT1 gene product operably linked to a promoter; and (b) recovery of a plant which contains said nucleotide sequence and has a modified inflorescence architecture compared to an unmodified plant. Preferably, the method involves nucleotide sequences encoding a peptide having at least 50%, preferably 70%, more preferably 90%, more preferably 95%, most preferably 99% homology to the peptide encoded by SEQ ID NO: 5 or 6, or a part thereof, or a complement thereof. Preferably, the method involves nucleotide sequences that are able to bind under stringent conditions to SEQ ID NO: 5 or 6, or a part thereof, or a complement thereof.

Preferably, the modification of inflorescence architecture comprises an altered pedicel, peduncle or style, and more preferably the altered pedicel has an altered length compared to an unmodified plant. Moreover, the modified inflorescence architecture preferably comprises downwardly pointing flowers.

In alternative embodiments, the invention provides methods characterised in that the nucleotide sequences are derived from a plant of the genus *Arabidopsis* or *Brassica* and/or the transformed plants are of the genus *Arabidopsis* or *Brassica* or are selected from the group consisting of: a dicot, a monocot, and a member of Cruciferae.

Preferably, the methods of the invention can generate a plant having either a compact or an open inflorescence compared to an unmodified plant. The nucleotide sequences may be expressed in a sense direction for complementary inhibition of an endogenous KNAT1 gene in the transgenic plant, such that the plant has a compact inflorescence architecture compared to an unmodified plant. Preferably, the KNAT1 gene may be in a mutated form. In an alternative embodiment, the nucleotide sequence may be expressed in an antisense direction for antisense inhibition of an endogenous KNAT1 gene such that the plant has a compact inflorescence architecture and/or decreased pedicel length compared to an unmodified plant. In an further alternative embodiment, the nucleotide sequence may be overexpressed in a sense direction, such that the plant has an open inflorescence architecture and/or increased pedicel length compared to an unmodified plant.

In one aspect, the plant may harbour a bp mutation such that expression of said nucleotide sequence is complementary to said mutation, inducing the plant exhibit a wild-type phenotype.

The promoters for use in accordance with the methods of the present invention may take various forms. For example, the promoter may comprise, in one embodiment a transcriptional regulatory region normally in operable association with an endogenous KNAT1 gene or homologue thereof. Alternatively, the promoter may comprise a transcriptional regulatory region that is not normally in operable association with an endogenous KNAT1 gene or homologue thereof. Further, the promoter may be selected from the group consisting of: a constitutive promoter, an inducible promoter, an organ specific promoter, a strong promoter, a weak promoter, and an endogenous KNAT1 promoter from *Arabidopsis*. Alternatively, the promoter may be derived from a functional portion of SEQ ID NO: 23 or SEQ ID NO: 24.

The present invention further encompasses methods for modifying the infloresence architecture of a plant involving the use of sequences homologous to SEQ ID NO: 5 or 6, such as, for example, SEQ ID NOS: 11, 14, 15, and 20.

In another embodiment, the present invention provides a method of identifying a plant that has been successfully transformed with a construct, characterised in that the method comprises the steps of: (a) introducing into plant cells capable of being transformed and regenerated into whole plants a construct comprising, in addition to the DNA sequences required for transformation and selection in plants, a nucleotide sequence derived from a KNAT1 gene and encoding at least part of a KNAT1 gene product, operably linked to a promoter; ((b) regenerating said plant cells into whole plants; and (c) inspecting the inflorescences of said plants to determine those plants successfully transformed with said construct, and expressing said nucleotide sequence. In a preferred embodiment, the plant cells and the regenerated whole plants harbour a bp mutation, and successful transformation and expression of said nucleotide sequence complements said mutation, thereby generating a plant exhibiting a wild-type phenotype. More preferably, the construct is bicistronic and further comprises a second DNA expression cassette for generating a transcript unrelated to said nucleotide sequence derived from a KNAT1 gene. In this way, the KNAT1-related portion of the construct can complement a known mutation in a plant and positively confirm transformation, and simultaneously a second transcript can be produced from a second region of the bicistronic construct, conferring desirable or otherwise properties to the transgenic plant.

The present invention further encompasses transgenic plants generated by any of the methods of the present invention. In this regard, the transgenic plants are preferably of the genus *Arabidopsis* or *Brassica* or plants selected from the group consisting of: a dicot, a monocot, and a member of Cruciferae. Moreover, the exogenous DNA or construct introduced into the plant may preferably be derived from plants of the genus *Arabidopsis* or *Brassica*.

The transgenic plants of the present invention preferably comprise a modified inflorescence (e.g. compact or open) compared to an unmodified plant. Preferably the modified inflorescence architecture comprises an altered pedicel, peduncle or style, more preferably a plant with altered pedicel length or downwardly pointing flowers compared to an unmodified plant.

The present invention further encompasses, in other embodiments, isolated nucleotide sequences for generating a transgenic plant with modified inflorescence architecture, characterised in that the isolated nucleotide sequences are derived from a KNAT1 gene and encode at least part of a KNAT1 gene product. The isolated nucleotide sequences preferably comprise a sequence selected from: (a) SEQ ID NO: 5 or 6, or a part thereof, or a complement thereof; and (b)

a nucleotide sequence encoding a peptide having at least 50%, preferably 70%, more preferably 90%, more preferably 95%, and most preferably 99% homology to the peptide encoded by the nucleotide sequence defined in (a).

Preferably the isolated nucleotide sequences of the present invention are characterised in that the nucleotide sequences hybridise under stringent conditions to the nucleotide sequence of SEQ ID NO: 5 or 6, or a part thereof or a complement thereof. The isolated nucleotide sequences for generating a transgenic plant with a modified inflorescence architecture compared to an unmodified plant, include sequences derived from a construct selected from the group consisting of: pRD400-951/955, pRD400-951/956, pRD400-35S::AtBPS, pRD400-35S::AtBPA/S, pRD400-35S::Atbp-2, pRP400-951/952::Atbp-2, pRD400-951/952::BnBPS, pRD400-35S::BnBPS, and pRD400-35S::BnBPA/S.

The present invention further encompasses, in further embodiments, the use of isolated nucleotide sequences related to the KNAT1 gene, for generating a transgenic plant with a modified inflorescence architecture.

BRIEF DESCRIPTIONS OF THE DRAWINGS

FIG. 1. Illustration of the bp BP phenotype in *Arabidopsis*. In this figure the phenotypes of 6 week-old Ler wt, bp-1 Ler and bp-2 Ler plants. (A) Whole plant. Close-up of floral nodes with siliques of Ler wt (B) and bp-1 Ler (C). Close-up of inflorescence apex in Ler wt (D) and bp-1 Ler (E).

Figure 2:
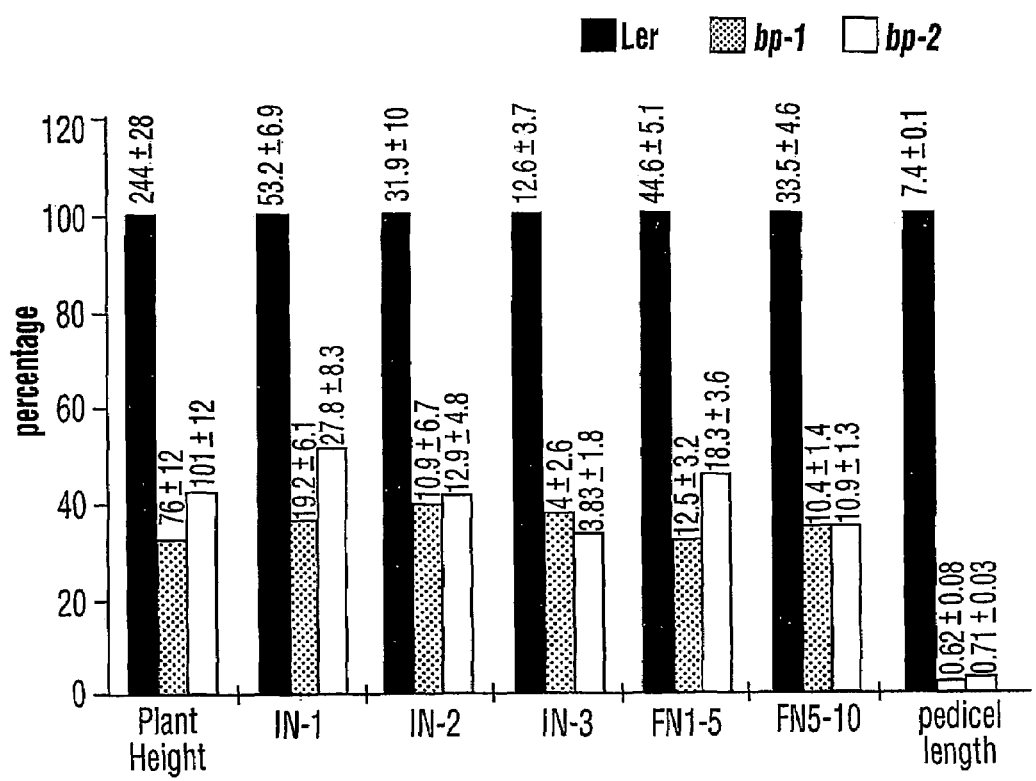

FIG. 2. A comparison of internode and pedicel lengths between Ler wt, bp-1 Ler and bp-2 Ler. The histograms represent the percentage reduction in pedicel length for bp-1 and bp-2; the actual measurements in mm (mean values±standard deviation of 30 data points) are shown above, the corresponding bars. The average pedicel lengths represent the values for the floral nodes 1-5. IN-1, IN-2, IN-3: coflorescence nodes 1, 2, 3; FN1-5: floral nodes 1-5; FN6-10: floral nodes 6-10.

Figure 3:
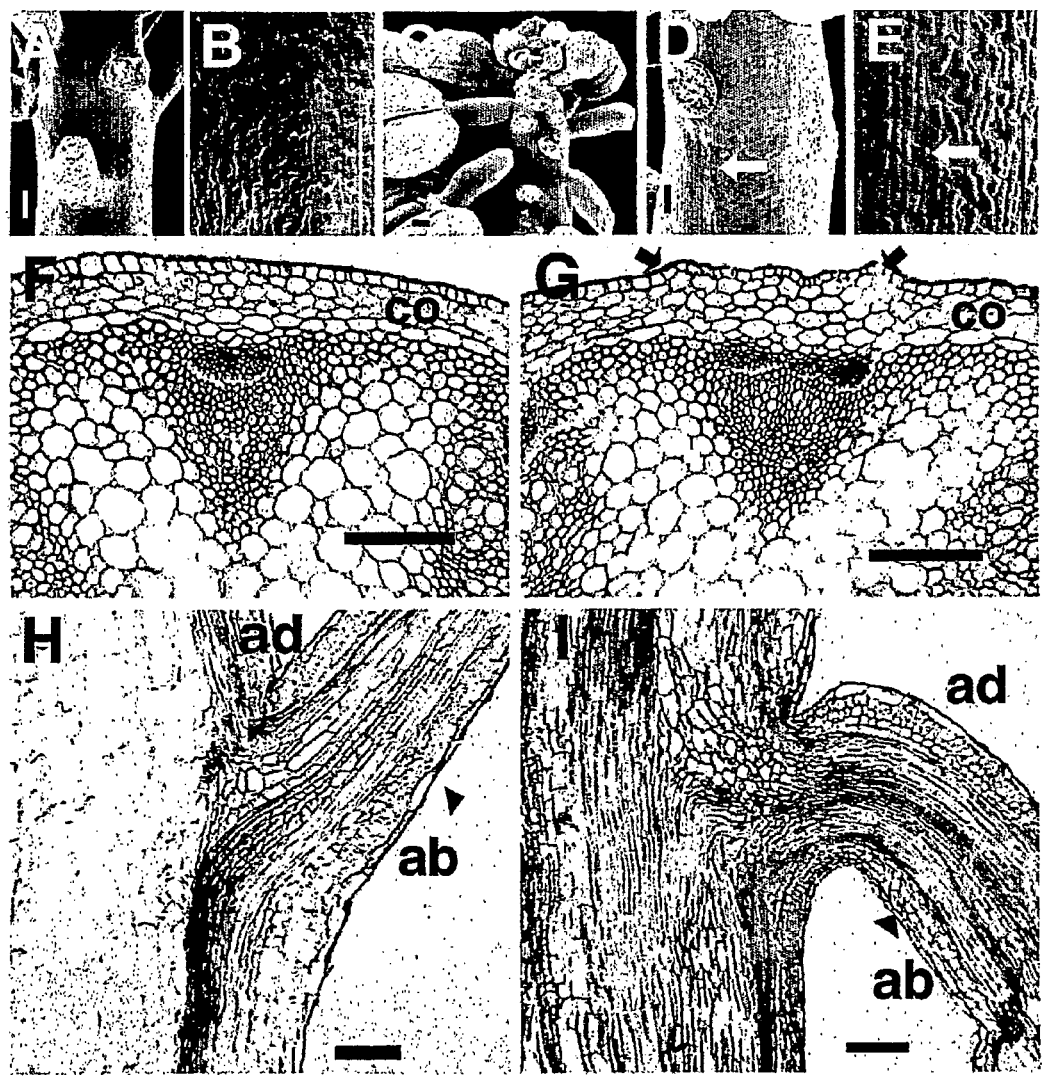

FIG. 3. SEM micrographs of inflorescences from Ler (A,B) and bp-1 Ler (C-E). (A) Ler wt floral nodes. (B) Ler wt peduncle internode magnified to show differentiated epidermal cells. (C) bp-1 floral nodes. (D,E) bp-1 peduncle internode showing stripes of less differentiated epidermal cells (arrows) that originate below the node. Anatomy of the peduncle of Ler wt (F,H) and bp-1 (G,I). Cross sections through the internodal region of the peduncle of Ler wt (F) and bp-1 (G). Longitudinal sections through the nodal region of Ler wt (H) and bp-1 (I). Arrows in G demarcate a band of less differentiated cells that originate below the node. co, cortical cell layer; ad, adaxial; ab, abaxial. Bar=0.1 mm (A,B, D,E-I); 1 mm (C).

Figure 4:
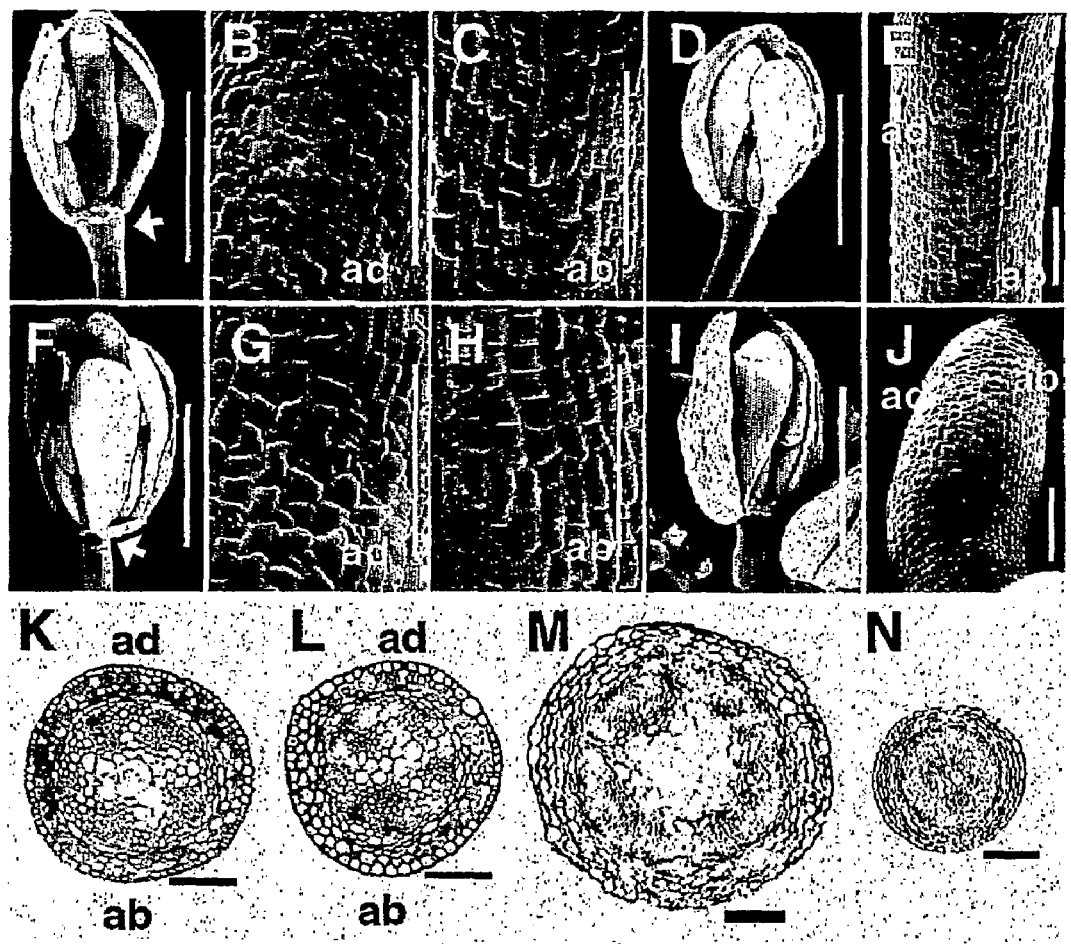

FIG. 4. Pedicel development in Ler wt (A-E, K,L) and bp-1 Ler (F-J, M,N). SEM of pedicel of stage 12 flower of Ler wt (A) showing complete epidermal cell differentiation on both the adaxial (B) and abaxial (C) sides. Pedicel of stage 12 flower of bp-1 (F) with narrow distal end (←), differentiated adaxial (G) and less differentiated abaxial (H) sides. SEM of stage 13 flower of Ler wt (D) and its pedicel (E). Stage 13 flower of bp-1 (I) and its pedicel (J) showing less differentiated abaxial side. Cross section through the mid-region of the pedicel of Ler wt (K) and bp-1 (L) and the distal end of the pedicel of Ler wt (M) and bp-1 (N). Bar=1 mm (A,D,F,I); 0.1 mm (B,C,E,G,H,J-N). ad, adaxial; ab, abaxial.

Figure 5:
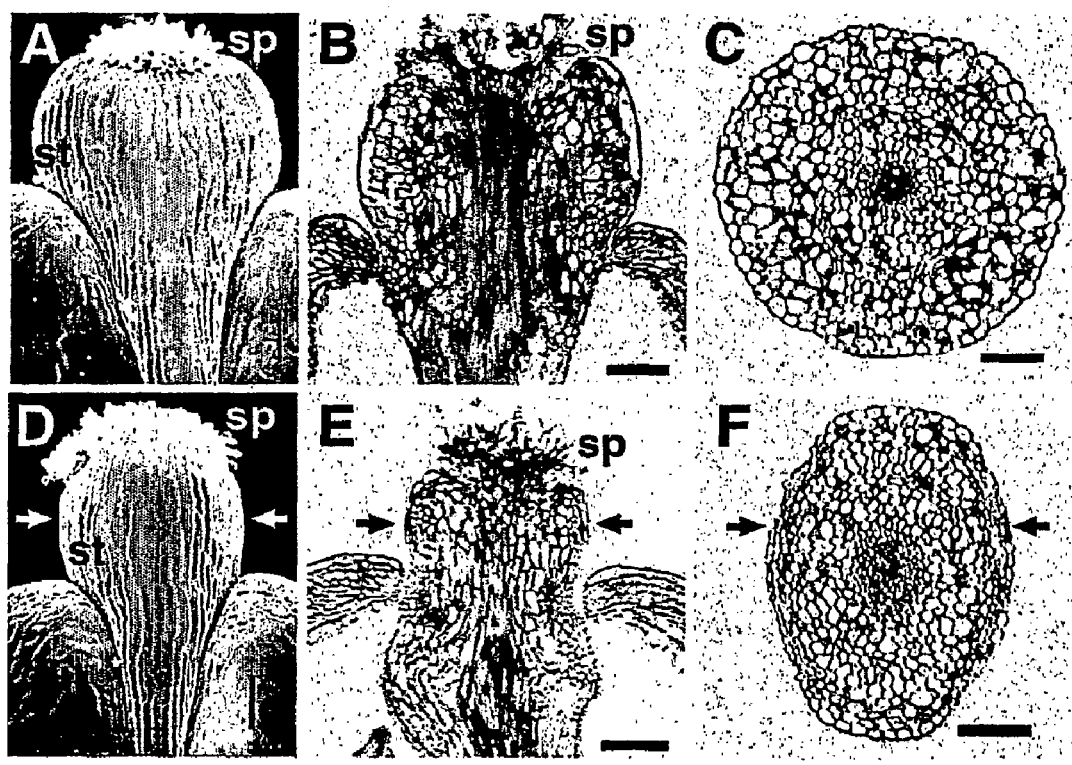

FIG. 5. SEM of the style of a stage 17 flower of Ler wt (A), and bp-1 Ler (D). Longitudinal sections through the style of Ler (B) and bp-1 (E). Cross sections through the style of Ler wt (C) and bp-1 (F). Arrows in D-F indicate the lateral axis. Bar=0.1 mm. sp, stigmatic papillae; st, style.

Figure 6:
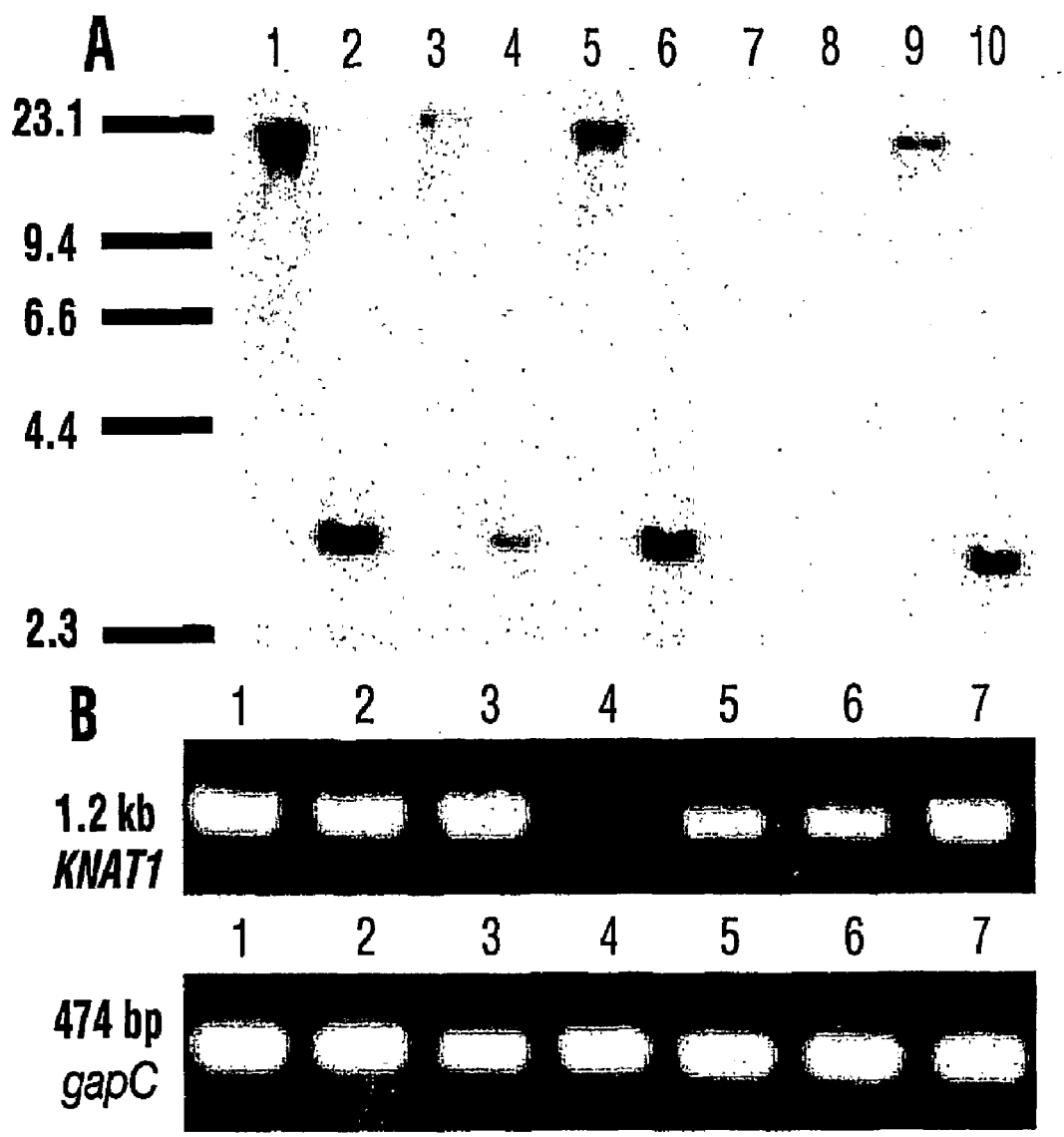

FIG. 6. Southern blot and RT-PCR of KNAT1. (A) Southern blot. Genomic DNA from Col wt (lanes 1 and 2), Ler wt (lanes 3 and 4), RLD wt (lanes 5 and 6), bp-1 Ler (lanes 7 and 8), and bp-2 RLD (lanes 9 and 10) was digested with BamHI (lanes 1, 3, 5, 7, 9) or EcoRI (lanes 2, 4, 6, 8, 10) and probed with the KNAT1 cDNA. Sizes of the MW standards (kb) are indicated. (B) RT-PCR using KNAT1 primers 954 and 955. Lane 1, Col wt; lane 2, RLD wt; lane 3, Ler wt; lane 4, bp-1 Ler; lane 5, bp-2 Ler; lane 6, bp-2 RLD; lane 7, bp-2 Col. The same cDNA pools were amplified with primers specific for gapC.

FIG. 7. Sequences of the polymorphic regions of the BP-encoding cDNAs from Col wt, RLD wt, Ler wt, and bp-2 (SEQ ID No. 6). Numbering is shown for the Col wt sequence (GenBank U14174). Stop codons are indicated by an asterisk (*), nucleotide and 25 amino acid deletions relative to Col wt are indicated by a dash (—), and nucleotide and amino acid insertions relative to Col wt are indicated in parentheses ( ). The C-T transition that causes a stop codon at position 535 in bp-2 is shown in bold. Nucleotides downstream of position 540 were identical among all of the BP-encoding genes analyzed and are not shown.

Figure 8:
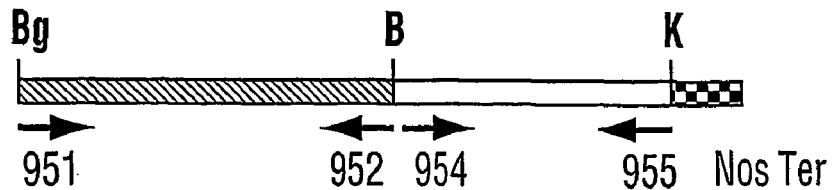

FIG. 8. Vector map of the plant transformation vector referred to as pRD400-951/955, comprising of the KNAT1 cDNA cloned downstream of the putative KNAT1 promoter.

Figure 9:

FIG. 9. Vector map of the plant transformation vector referred to as pRD400-951/956, consisting of the putative KNAT1 promoter and the KNAT1-encoding ORF amplified from genomic DNA.

Figure 10:
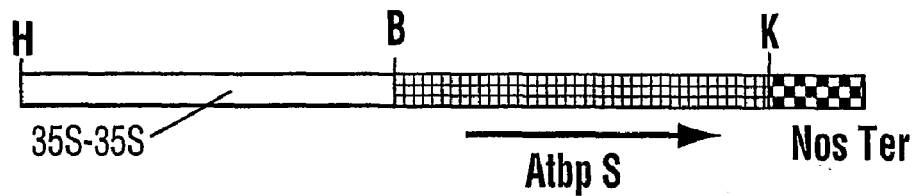

FIG. 10. Vector map of the plant transformation vector referred to as pRD400-35S::AtBPS, consisting of the *A. thaliana* BP ORF under the control of the 35S promoter.

Figure 11:
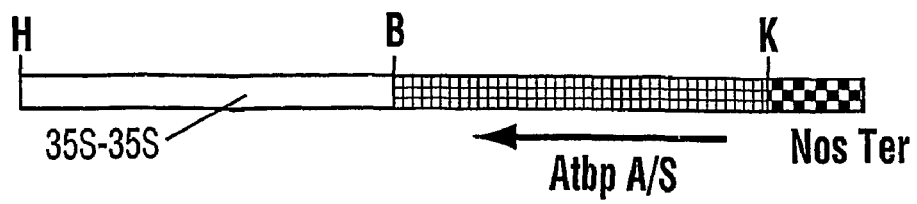

FIG. 11. Vector map of the plant transformation vector referred to as pRD400-35S::AtBPA/S, consisting of the *A. thaliana* BP ORF in an antisense orientation under the control of the 35S promoter.

Figure 12:
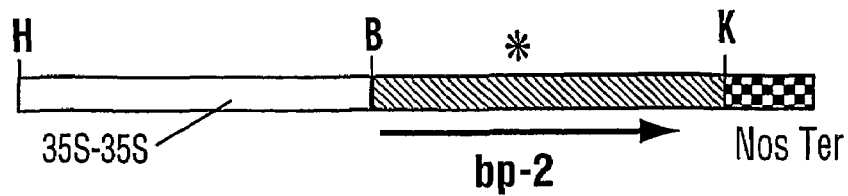

FIG. 12. Vector map of the plant transformation vector referred to as pRD400-35S::Atbp-2, consisting of the altered BP gene coding sequence (SEQ ID. NO: 6) under the control of the 35S promoter. The asterisk denotes the approximate location of the stop codon that results in a truncated predicted protein.

Figure 13:
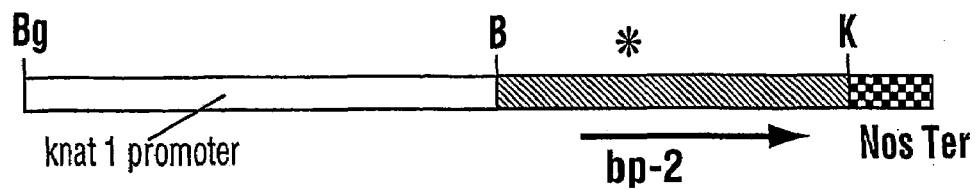

FIG. 13. The vector pRD400-951/952::Atbp-2, consisting of the *A. thaliana* bp-2 cDNA under the control of the *A. thaliana* KNAT1 promoter. The asterisk denotes the approximate location of the stop codon that results in a truncated predicted protein.

Figure 14:
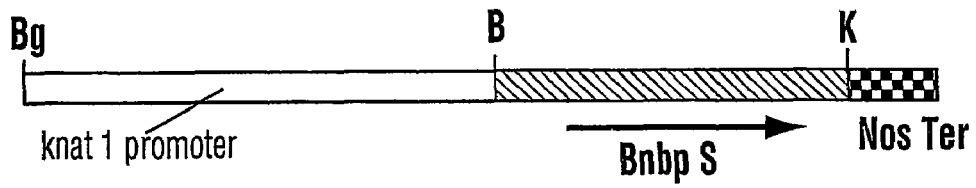

FIG. 14. The map of the vector of pRD400-951/952::Bn-BPS, consisting of the *B. napus* BP ORF (SEQ ID. NO: 11) under the control of the *A. thaliana* KNAT1 promoter.

Figure 15:
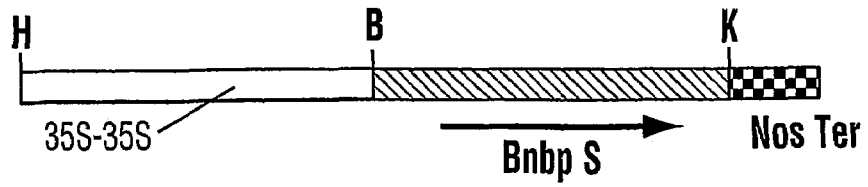

FIG. 15. The vector map of pRD400-35S::BnBPS, consisting of the *B. napus* BP ORE (SEQ ID NO: 11) under the control of an optimized cauliflower mosaic virus (CaMV) 35S promoter.

Figure 16:
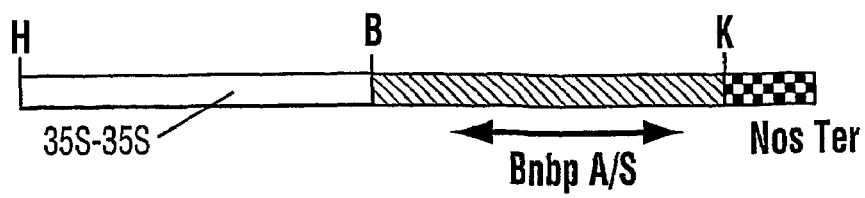

FIG. 16. The vector map pRD400-35S::BnBPA/S, consisting of the *B. napus* BP ORF (SEQ ID NO: 1) in an antisense orientation under the control of the 35S promoter.

DETAILED DESCRIPTION OF THE INVENTION

Definitions

The singular forms "a," "an," and "the" include plural reference unless the context clearly dictates otherwise.

A "coding sequence" or "coding region" is the part of a gene that codes for the amino acid sequence of a protein or for a functional RNA such as a tRNA or rRNA. A coding sequence typically represents the final amino acid sequence of a protein or the final sequence of a structural nucleic acid. Coding sequences may be interrupted in the gene by intervening sequences, typically intervening sequences are not found in the mature coding sequence.

A "polynucleotide encoding an amino acid sequence" refers to a nucleic acid sequence that encodes the genetic code of at least a portion of a mature protein sequence, typically a contiguous string of amino acids typically linked through a peptide bond. An "amino acid sequence" is typically two or more amino acid residues, more typically 10 or more amino acids in a specific defined order.

A "complement" or "complementary sequence" is a sequence of nucleotides which forms a hydrogen-bonded duplex with another sequence of nucleotides according to Watson-Crick base-pairing rules. For example, the complementary base sequence for 5'-AGCT-3' is 3'-TCGA-5'.

"Expression" refers to the transcription of a gene into structural RNA (rRNA, tRNA) or messenger RNA (mRNA) with subsequent translation into a protein in the case of then mRNA.

Polynucleotides are "functionally equivalent" if they perform substantially the same biological function. By substantially the same biological function it is meant that similar protein activities or protein function are encoded by a mRNA polynucleotide, or a structural polynucleotide has a similar structure and biological activity.

Polynucleotides are "heterologous" to one another if they do not naturally occur together in the same arrangement in the same organism. A polynucleotide is heterologous to an organism if it does not naturally occur in its particular form and arrangement in that organism.

Polynucleotides or polypeptides have "homologous" or "identical" sequences if the sequence of nucleotides or amino acid residues, respectively, in the two sequences is the same when aligned for maximum correspondence as described herein. Sequence comparisons between two or more polynucleotides or polypeptides are generally performed by comparing portions of the two sequences over a portion of the sequence to identify and compare local regions. The comparison portion is generally from about 20 to about 200 contiguous nucleotides or contiguous amino acid residues or more. The "percentage of sequence identity" or "percentage of sequence homology" for polynucleotides and polypeptides, such as 50, 60, 70, 80, 90, 95, 98, 99 or 100 percent sequence identity may be determined by comparing two optimally aligned sequences which may or may not include gaps for optimal alignment over a comparison region, wherein the portion of the polynucleotide or polypeptide sequence in the comparison may include additions or deletions (i.e., gaps) as compared to the reference sequence (which does not comprise additions or deletions) for optimal alignment of the two sequences.

The percentage of homology or similarity is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al 1990. J. Mol. Biol. 215:403; Altschul, S. F. et al 1997. Nucleic Acids Res. 25: 3389-3402) and ClustalW programs. Other suitable programs include GAP, BESTFIT, FASTA, and TFASTA in the Wisconsin Genetics Software Package (Genetics Computer Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTX program, available as described above.

Sequence identity typically refers to sequences that have identical residues in order, whereas sequence similarity refers to sequences that have similar or functionally related residues in order. For example an identical polynucleotide sequence would have the same nucleotide bases in a specific nucleotide sequence as found in a different polynucleotide sequence. Sequence similarity would include sequences that are similar in character for example purines and pyrimidines arranged in a specific fashion. In the case of amino acid sequences, sequence identity means the same amino acid residues in a specific order, where as sequence similarity would allow for amino acids with similar chemical characteristics (for instance basic amino acids, or hydrophobic amino acids) to reside within a specific order.

The terms "stringent conditions" or "stringent hybridization conditions" includes reference to conditions under which a probe will hybridize to its target sequence, to a detectably greater degree than other sequences (e.g. at least 2-fold over background). Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH at which 50% of a complementary target sequence hybridizes to a perfectly matched probe. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C. Hybridization procedures are well-known in the art and are described in Ausubel et al.,(Ausubel F. M., et al.,1994, Current Protocols in Molecular Biology, John Wiley & Sons Inc.).

"Isolated" refers to material that is: (1) substantially or essentially free from components which normally accompany or interact with it as found in its naturally occurring environment; or (2) if in its natural environment, the material has been non-naturally altered to a composition and/or placed at a locus in the cell not native to a material found in that environment. The isolated material optionally comprises material not found with the material in its natural environment. For example, a naturally occurring nucleic acid becomes an isolated nucleic acid if it is altered, or if it is transcribed from DNA which is altered, by non-natural, synthetic methods performed within the cell from which it originates.

Two DNA sequences are "operably linked" if the linkage allows the two sequences to carry out their normal functions relative to each other. For instance, a promoter region would be operably linked to a coding-sequence if the promoter were capable of effecting transcription of that coding sequence and said coding sequence encoded a product intended to be expressed in response to the activity of the promoter.

A "polynucleotide" is a sequence of two or more deoxyribonucleotides (in DNA) or ribonucleotides (in RNA).

A "DNA construct" is a nucleic acid molecule that is isolated from a naturally occurring gene or which has been modified to contain segments of nucleic acid which are combined and juxtaposed in a manner which would not normally otherwise exist in nature.

A "polypeptide" is a sequence of two or more amino acids.

A "homeobox" gene is a gene that is typically involved the developmental process of an organism, and usually contains one or more specific regions within the encoded protein that include a DNA binding region and a second region that is distinct from the binding region. Homeobox genes typically contain a homoedomain that is homologous or has similarity to other homeodomain found in other homeobox genes.

A "promoter" or transcriptional regulatory region is a cis-acting DNA sequence, generally located upstream of the initiation site of a gene, to which RNA polymerase may bind and initiate correct transcription.

A "recombinant" polynucleotide, for instance a recombinant DNA molecule, is a novel nucleic acid sequence formed through the ligation of two or more nonhomologous DNA molecules (for example a recombinant plasmid containing one or more inserts of foreign DNA cloned into it).

"Transformation" means the directed modification of the genome of a cell by the external application of recombinant DNA from another cell of different genotype, leading to its uptake and integration into the subject cell's genome.

A "transgenic plant" encompasses all descendants, hybrids, and crosses thereof, whether reproduced sexually or asexually, and which continue to harbour the foreign DNA.

An inflorescence is a portion of a flowering plant that produces and supports flower development and typically seed formation. An inflorescence is usually formed from a meristem structure. The terms "inflorescence" and "flowering stalk" are used interchangeably herein.

Unless defined otherwise all technical and scientific terms used herein have the same meaning as commonly understood to one of ordinary skill in the art to which this invention belongs.

The present application describes nucleic acids encoding a gene from *Arabidopsis* referred to as the BP gene, or the gene encoding the *brevipedicellus* phenotype, and the role of said gene in determining inflorescence morphology. Said gene is a member of the KNOXgene family in *Arabidopsis* that is involved in control of certain aspects of flower development. The gene identified in the present invention represents an altered form of the wild-type gene. As a result of the present discovery, it was found that the wild-type gene is normally involved in the control of the architecture of the inflorescence or at least the pedicel, peduncle and style structures within the inflorescence.

The gene sequences responsible for the bp phenotype have not been previously identified and hence the molecular nature of the bp mutation was not known prior to this disclosure. Accordingly, the utility of the bp mutation for practical purposes has not been described. The present invention identifies the molecular basis of the bp mutation and methods for using the gene encoded by the BP locus in alteration of plant inflorescence structure.

The present application further describes the discovery that the alteration in the expression levels of said gene, in particular the reduction in expression of said gene, or expression of an altered protein form of said gene results in changes in the inflorescence structure. Loss of function of said gene results in a compact inflorescence structure with changes in the length of the internodes, pedicle length and angle of seed pod attachment. The invention also provides evidence that gain of function can restore a wild-type phenotype, hence providing direction on alteration of inflorescence structure towards a compact structure or a structure that exhibits a less compact, more spread out structure.

The present application further describes the molecular basis of two loss of function alterations, providing a basis for the engineering of altered inflorescence architecture. In the present invention, the methods for the alteration of inflorescence architecture were shown to be: loss of the expression of the gene itself (inhibition of gene expression); and loss of function by expression of an altered form of the protein (expression of altered protein). Accordingly, it is anticipated that the engineering of similar loss of function phenotypes in numerous flowering plant species can be easily and routinely accomplished by the use of methods described herein to identify, modify and alter the expression of the normally encoded gene or genes related to said nucleic acid sequences described herein. Thus, the present invention encompasses plants with altered inflorescence structures, in particular plants with an altered pedicel, peduncle or style can be obtained, alone or in combination, to produce an altered inflorescence structure.

Portions of the gene sequence representing the native wild-type protein coding sequence described in the present invention were found to be identical to the previously identified homeobox gene called KNAT1, but the involvement of the KNAT1 gene in the control of the inflorescence architecture or its association with the bp phenotype have not previously been described nor anticipated. Indeed, the previous studies (Lincoln et al, Plant Cell, 6: 1859-1876, 1994) on the KNAT1 gene expression failed to identify a primary role for the gene in inflorescence architecture, suggesting that the expression of the KNAT1 gene was restricted in its expression in the inflorescence. No indication of the role of KNAT1 in peduncle, pedicle or style formation was suggested. Efforts to determine the function of the KNAT1 gene in this study were restricted to ectopic constitutive expression of the KNAT1 native coding sequence. No loss of function information for the KNAT1 was provided hence no definition of the nature of the activity of KNAT1 could be inferred from these studies. Accordingly the art did not describe a function for the KNAT1 gene, nor for that matter link the expression of the KNAT1 gene with the bp mutant.

The present invention has thus assigned function to the KNAT1 gene, identified altered forms of the KNAT1 gene as the basis of the BP phenotype and provides methods for the alteration of wild-type gene expression to produce altered inflorescence, in particular inflorescence structures with alterations in the peduncle, pedicel or style or combinations thereof.

The present invention encompasses the use of the KNAT1 gene, and parts thereof, complements thereof, and homologues thereof, for generating transgenic plants with altered inflorescence structures. The present invention also encompasses the use of nucleic acid sequences encoding peptides having at least 50% homology, preferably 70% homology, preferably 90%, more preferably 95%, most preferably 99% to the peptides encoded by the KNAT1 gene or SEQ ID NOS: 5 and 6. In this regard, homologous proteins with at least 50% or 70% predicted amino acid sequence homology are expected to encompass proteins with activity as those defined by the present invention, wherein disruption of expression or overexpression of the homologous proteins is expected to generate plants with altered structure as described in the present application. Such proteins may be derived from similar or unrelated species of plant.

The present invention also encompasses polynucleotide sequences encoding peptides comprising at least 90%, 95% or 99% sequence homology to the peptides encoded by the KNAT1 gene or SEQ ID NOS: 5 and 6. This class of related proteins is intended to include close gene family members with very similar or identical catalytic activity. In addition, peptides with 90% to 99% amino acid sequence homology may be derived from functional homologues of similar species of plant, or from directed mutations to the sequences disclosed in the present application.

The present invention demonstrates the utility of said nucleic acid sequences and altered forms of the protein encoded by said nucleic acid sequences in controlling inflorescence development and hence assigns a novel utility for the use of the KNAT1 gene, and homologues thereof; to alter floral structure in flowering plants.

The nucleic acid sequences provided in the present invention can be used to alter plant morphology by heterologous expression, for example, of the nucleic acid sequences shown in SEQ ID. NOS: 5 and 6 and other homologous sequences as described herein.

The nucleic acid sequence of SEQ ID. NO: 5 encodes a KNAT1 protein that has been shown in the present invention to be involved in maintaining the normal development of an inflorescence of a flowering plant, wherein expression of the protein confers the normal architecture of the inflorescence of a flowering plant. The protein represents a member of the homeodomain proteins involved in the control of plant development.

The nucleic acid sequence of SEQ ID NO: 6 encodes an altered form of the KNAT1 protein, herein referred to as the BP related protein that is preferentially expressed in the inflorescence of a flowering plant, wherein expression of the protein influences the architecture of the inflorescence of a flowering plant. This protein represents an altered member of the homeodomain proteins involved in the control of plant development.

The present invention encompasses the expression of nucleotide sequences derived from the KNAT1 gene, including SEQ ID Nos. 5 and 6 or homologues thereof to alter the inflorescence of a flowering plant by using said polynucleotides to alter the expression of the protein normally expressed by KNAT1 and related genes using methods familiar to those of skill in the art.

In one aspect of the present invention, a gene sequence is used to modify the architecture of a inflorescence in a flowering plant by heterologous expression of the coding sequence of SEQ ID. NO: 6 or parts thereof, or complements thereof, or homologues thereof.

In another aspect of the present invention, one or more portions, of at least 50 amino acids, but less than 400 amino acids, most preferably about 179 amino acids of the protein encoded by the nucleic acid sequence of SEQ ID. NO: 6 are expressed in a host plant, said expression causing the alteration of inflorescence architecture as illustrated herein.

In another aspect of the present invention, the nucleic acid sequence, or coding region thereof described in the KNAT1 gene or in SEQ ID NO: 5 or 6 can used to modify the inflorescence of a flowering plant by using said sequence to isolate a homologous nucleic acid that encodes a protein that is at least 50% homologous to the protein encoded by SEQ ID. NO: 6 and expressing said homologous nucleic acid as part of a recombinant DNA construct in a host plant species. The recombinant DNA construct so expressed is engineered to express an altered form of the wild-type protein, or engineered to reduce the expression of the wild-type gene. Method for the identification and isolation of homologous DNA sequences are very well known in the art and are included, for example in Sambrook et al., *Molecular Cloning: A Laboratory Manual*, Cold Spring Harbor Press, Cold Spring Harbor, N.Y. (1989).

It will also be understood to a person of skill in the art that site-directed mutagenesis techniques are readily applicable to the polynucleotide sequences of the present invention, to make the sequences better suited for use in generated morphologically modified transgenic plants. Related techniques are well understood in the art, for example as provided in Sambrook et al., *Molecular Cloning: A Laboratory Manual*, Cold Spring Harbor Press, Cold Spring Harbor, N.Y. (1989). In this regard, the present invention teaches the use of nucleotide sequences derived from the KNAT1 gene, including, for example SEQ ID NOS: 5 and 6. However, the present invention is not intended to be limited to these specific sequences. Numerous directed mutagenesis techniques would permit the non-informed technician to alter one or more residues in the nucleotide sequences, thus changing. The subsequently expressed polypeptide sequences. Moreover, commercial 'kits' are available from numerous companies that permit directed mutagenesis to be carried out (available for example from Promega and Biorad). These include the use of plasmids with altered antibiotic resistance, uracil incorporation and PCR techniques to generate the desired mutation. The mutations generated may include point mutations, deletions and truncations as required. The present invention is therefore intended to encompass corresponding mutants of the KNAT1 gene, both cDNA and genomic DNA sequences in accordance with the teachings of the present application.

The polynucleotide sequences of the present invention must be ligated into suitable vectors before transfer of the genetic material into plants. For this purpose, standard ligation techniques that are well known in the art may be used. Such techniques are readily obtainable from any standard textbook relating to protocols in molecular biology, and suitable ligase enzymes are commercially available.

In another aspect of the present invention, the KNAT1 gene sequence, and parts, complements, and homologues thereoofare used to modify a plant inflorescence by the transformation of plant cells with a plant transformation vector comprising a coding, for example, a region of said nucleic acid described in SEQ ID. NO: 6 under the control of a heterologous or native/homologous promoter.

In another aspect of the present invention, the nucleic acid sequence described in SEQ ID. NO: 6 is used to modify plant inflorescence architecture by the transformation of plant cells with a plant transformation vector comprising a coding region of said polynucleotide under the control of the promoter normally-associated with the nucleic acid sequence found in SEQ ID NO: 6.

In one aspect of the present invention, the nucleic acid described in SEQ ID NO: 6 is used to alter the phenotype of an *Arabidopsis* plant by introduction of said nucleic acid or portion thereof into an *Arabidopsis* plant and recovering a plant wherein the inflorescence architecture of the plant has changed as a result of the introduction of the nucleic acid sequence, or portion thereof into the plant.

In one aspect of the invention these nucleic acid sequences may be used for identification of related homologous sequences deposited in public databases through comparative techniques well-known in the art, or as a hybridization probe for the idenitification of related cDNA or genomic sequences from various species, including plant species where the DNA sequence information is not known. In particular it is contemplated that these sequences so described can be used for the isolation of plant genes encoding similar activities.

In another aspect of the present invention, nucleic acids encoding a protein at least 50% homologous to the protein encoded by SEQ ID. NO: 6 are isolated and said nucleic acids are used to alter the phenotype of the inflorescence of the plant species from which they were derived by introduction of said nucleic acid or portion thereof into said plant species and recovering a plant wherein the inflorescence architecture of the plant has changed as a result of the introduction of the nucleic acid sequence, or portion thereof into the plant species.

In another aspect of the present invention, said nucleic acids that encode a protein at least 50% homologous to the protein encoded by SEQ ID. NO: 6 are used to alter the inflorescence architecture of a flowering plant by introduction of said nucleic acid into a plant species heterologous to the plant species from which said nucleic acid sequence was derived.

In yet another aspect of the present invention, the nucleic acid sequence described in SEQ ID. NO: 6 is used as a visible marker for plant transformation, said marker producing plants with an altered inflorescence architecture relative to plants not transformed with the same.

In order to isolate nucleic acid sequences involved in inflorescence architecture, mutant plant lines with altered inflorescence architecture were analyzed. A mutant in *Arabidopsis* designated as bp has been described that exhibits a significant reduction in pedicel length (~80-90%) along with shortening in the internodal regions (40-60%). The bp mutant was first described by Koornmeef et al in 1983 (ibid.) and has been used extensively in mapping studies as a classical chromosome 4 marker. However, no studies explaining the developmental or molecular basis of this mutation have been published to date.

In the present invention, mutant alleles of this gene were isolated by screening T-DNA insertional lines for bp phenotypes. A line was found that showed a bp mutant phenotype. As described herein, this isolated line was designated as bp-2 and the Koornneef isolate as bp-1. Thus, a new bp mutation was discovered by the present inventors.

In order to establish the basis of the new mutation, pure lines with single recessive alleles of bp-1 and bp-2 were established in *Arabidopsis* ecotypes Landsberg erecta (ter) and Columbia (col).

These lines were analyzed for architectural changes by Scanning Electron Microscopy (SEM) and the results indicated that epidermal cell differentiation is affected in both pedicel and internodes. Detailed SEM analysis of the pedicel showed that in the abaxial region (lower side), epidermal cell differentiation is more affected compared to the adaxial region (upper side) in addition to an overall reduction in cell divisions along the whole pedicel. Thus, the more pronounced abaxial changes in differentiation coupled with reduced cell division contribute to the change in the pedicel attachment angle and as a result produced shortened siliques (seed pods) pointing downwards in the BP mutant. This provides an architectural change in the morphology of the pedicel, leading to a plant with an altered inflorescence.

Cross sections through the internodal regions showed that in addition to alterations in epidermal cell differentiation, the sub-epidermal cortical region was changed in bp lines. In these lines, this region showed more intercellular spaces with larger cortical cells. Analysis of pedicel cross sections also revealed similar changes. Analysis of longitudinal sections through the nodes showed there were fewer cells (between floral nodes) in the bp lines compared to wild-type lines. The presence of fewer cells in the internodes is indicative of reduced cell divisions in this region, consistent with the significantly reduced internodal length in the bp lines.

The anatomical analysis clearly demonstrates that changes in cell-differentiation coupled with reduced cell division contributes to the altered, compact architectural phenotype in the bp lines. Accordingly, the changes in the architecture of the plant as a result of the BP mutation (or loss of its function) provide a new and valuable phenotype for flowering plants with a compact inflorescence and downward pointing seed pods.

Genetic analysis established that bp-2 is allelic to bp-1 previously mapped on chromosome 4. The bp-2 mutant phenotype is not physically linked to the T-DNA. The present inventors used a novel strategy of positional cloning to isolate the gene sequences associated with the bp phenotype.

The available genetic and recombination data suggest that the bp locus is located in between the marker DET2 and the centromere on chromosome 4. The genomic sequence corresponding to this region (~1.5 Mb) has been determined. To clone the BP gene, a region between DET1 and the centromere on chromosome 4 was chosen, based on genetic maps compiled from several data sets (http://www-*Arabidopsis*.org; (Pepper, A., Delaney, T., Washburn, T., Poole, D. & Chory, J. (1994) Cell 78). As the loss-of-function BP mutation mainly affects the pedicel and internodal regions but not the leaves, the BP transcripts are also likely differentially expressed. Probes corresponding to differentially expressed transcripts were prepared from the pedicel and internodal region and were used for subtraction hybridization with leaf-expressed transcripts to identify potential BP candidate genes from this ~1.5 Mb genomic region.

Radioactively labeled probes representing the transcripts preferentially expressed in the pedicel and internodal region were generated and hybridized the probes to restriction-digested overlapping BAC DNAs completely covering this region of chromosome 4. The results showed a single hybridizing band representing a ~20-kb BamHI fragment from BAC clone F9M13 (Mayer K F X, Schüller CME, et al. (1999) Sequence and analysis of chromosome 4 of the plant *Arabidopsis thaliana*. Nature 402:769-777.)

The annotation and BLAST analysis of this ~20 kb sequence showed only one potential gene, with 100% identity to the previously reported homeodomain containing protein KNAT1 (Lincoln, C., Long, J., Yamaguchi, J., Serikawa, K. & Hake, S. (1994) Plant Cell 6, 1859-1876.).

Previous reports in the art have mapped the KNAT1 gene to chromosome 5, however, the assignment of the chromosomal location of the KNAT1 gene has now been found to be in error. Utilizing the sequence comparison available based on screening the whole *Arabidopsis* genome demonstrated that the KNAT1 gene as well as the sequence of the BAC clone F9M13 containing the BP gene to be located on chromosome 4. Thus, it was established that the KNAT1 gene resides on chromosome 4, not 5 as previously reported.

This discovery shows that the previously described KNAT1 gene, formerly thought to be on chromosome 5 and encoding a protein previously thought to be involved in various facets of plant development, is the gene affected in the bp mutation and is in fact intimately involved in the control of inflorescence architecture.

Whereas the previous study with the KNAT1 gene demonstrated that overexpression of the coding region of the gene (cDNA) under CaMV 35S promoter produced several abnormal phenotypes including the ectopic production of meristems from adaxial (upper) surface of the leaves and altered leaf shape, the involvement of KNAT1 in pedicel architecture and control of inflorescence was not reported. The art failed to provide correlation between KNAT1 and the bp mutation herein described. Hence function of the KNAT1 gene was not assigned nor was the utility of the gene for controlling inflorescence architecture known or suggested. In addition, the chromosomal location of KNAT1 was also incorrectly reported further confusing the nature and utility of the KNAT1 gene.

However, as described herein, the second bp phenotype, bp-2 was unequivocally established as residing on chromosome 4 within the BAC F9M13 clone. Since the *brevipedicellus* (bp) mutation was described before the report of KNAT1, the inventors adopted the BP designation for this locus, according to conventional practice.

To determine if sequence differences existed between bp-1, bp-2 and wild type plants at the BP locus, a Southern blot with restriction digested genomic DNAs as target and the BP (KNAT1) cDNA as probe was carried out.

It was demonstrated that the bp-1 (Ler) lacks the BP (KNAT1) gene entirely, indicating that a deletion of this gene had occurred in this mutant. In contrast, bp-2 showed hybridizing bands similar to wild type. Thus bp-1 represents a deletion mutation of the BP gene, (or the KNAT1 gene) whereas bp-2 represents an alteration of the gene (and encoded protein) itself.

The expression of the BP transcripts in mutant and wt plants was analyzed. RT-PCR results confirm that bp-1 produces no BP transcript, while bp-2 produces an apparently full-length transcript comparable to the wild type. To identify the molecular basis for the bp-2 mutant phenotype, BP-encoding RT-PCR products from duplicate reverse transcription reactions using Ler (wt), RLD (wt), bp-2 (col), bp-2 (Ler), and bp-2 (RLD) were then cloned and their sequences determined.

In wt Ler and RLD the BP ORFs encoded predicted proteins of 400 amino acids, compared with a predicted protein of 398 amino acids for col wt. Minor sequence polymorphisms among the three wild-type BP cDNAs were detected, some of which resulted in differences in the predicted proteins. The BP gene, or KNAT1 gene contains two domains, a homeodomain, and an ELK region as typically found in plant and animal homeobox genes.

Changes were noted between wild-type and mutant BP proteins (bp-2 protein from Ler, col and RLD bp lines). In particular, the third and fourth asparagine/histidine-rich regions contained differing numbers of N residues among the three predicted proteins, which accounted for the differences in the total number of amino acids. The predicted BP proteins from bp-2 (col), bp-2 (Ler), and bp-2 (RLD) were identical and contained several unique polymorphisms compared with the wt sequences, hence the altered protein structure of the protein encoded by the bp-2 gene, confering altered functionality. This similarity between the different bp-2 proteins is expected since the original bp-2 mutation was introgressed into these three backgrounds. Interestingly, within the wt BP protein, minor polymorphisms were identified. Thus, protein polymorphisms are found in both wt and bp-2 proteins. For example, the third N-rich region contained only three N residues in the bp-2 lines, compared with five in col (wt) and six each in Ler (wt) and RLD (wt). Most importantly, bp-2 contained a C-T transition corresponding to position 535 of the col (wt) ORF. This point mutation changed codon 179 from cag to tag, thereby introducing a stop codon and resulting in a truncated predicted protein. The predicted BP protein of bp-2 is truncated upstream of both the important homeodomain and ELK regions, and as result this protein would not be expected to have normal function.

Further supporting evidence was obtained by transforming the bp-1 and bp-2 mutant lines with wild type BP genomic and cDNA constructs, which showed complementation of the mutant phenotype in transgenic plants and restoration of wild-type plant architecture.

In addition to simple complementation, control of inflorescence architecture can be regulated by expression levels of wt BP protein. The pedicels in col wt are much longer than Ler wt pedicels. Based on expression analysis, it was found that there is a 2-4 times higher transcript level of wt BP mRNA in col wt ecotype when compared to Ler wt, indicating that transcriptional regulation of BP contributes to the observed differences between these ecotypes. Thus, reducing the BP transcript levels can lead to a significant reduction in pedicel and internodal length. It is also desirable to increase the length of pedicel and/or internodes by up-regulating the expression of BP functional homologues. Thus, the results presented herein provide obvious strategies for the manipulation of inflorescence architecture.

Accordingly, the present invention ascribes a function to a previously identified homeobox gene, KNAT1, demonstrating that KNAT1 encodes a gene normally involved in the control of inflorescence development. This invention also demonstrates that KNAT1 is located on chromosome 4, not 5 as previously reported. In addition, this invention demonstrates the function of the KNAT1 gene in pedicel architecture and demonstrates alterations in the coding sequence of the KNAT1 gene can lead to a bp phenotype, thus establishing KNAT1 as the BP gene.

For the purposes of the present invention, nucleic acid sequences encoding a protein with substantial homology of 50% or more to the protein encoded by Seq ID. NO: 5, said proteins at least differentially expressed in the inflorescence of a flowering plant, and having a role in regulating in florescence architecture, are herein referred to as "BP" coding sequences, encoding a "BP" protein. Hence a "BP gene" from a flowering plant represents a coding sequence substantially similar to the Seq ID. NO: 5 in both protein sequence and protein function.

A "BP" gene may or may not include the 5' and 3' regions normally associated with said coding sequence, as a native "BP" gene will include at least functional portion of these regulatory regions, whereas a recombinant "BP" gene will have at least one portion of the 3' or 5' regions altered by the addition of new DNA sequences. The alteration of the 5' or 3' regions of said BP gene will be at least expected to cause altered expression in the native plant species from which the BP gene was derived when compared to the expression of the wt BP gene normally found in said plant species.

In one embodiment of the present invention, the expression of the BP gene in a plant species is altered by the inhibition of expression of the native BP gene coding sequence. Accordingly, it is one object of the present invention to alter the expression levels of the protein encoded by the BP gene normally found in a plant species by introduction of a recombinant BP gene that alters the expression of the wt BP gene by reduction of the native BP gene expression and reduction of the levels of the protein encoded by the wt BP gene in said plant species.

It is a further embodiment of the present invention to alter the expression of a wt BP gene in a plant species by introduction of a recombinant version of said BP gene, said recombinant version altered by the addition of one of more DNA sequences that lead to the increased expression of said gene relative to the expression of the wt BP gene in said plant species, leading to the increased expression levels of the protein encoded by a wt BP gene coding sequence in said plant species.

It is still another embodiment of the present invention to express a non-native BP coding sequence in a plant species. Said non-native BP coding sequence can be an altered form of the BP coding region normally found in said plant species, or a BP functional homologue from a different plant species. Expression of the non-native BP protein can be expected to alter the activity of the native BP protein by competition for DNA binding regions, or the non-native BP protein can encode an activity that provides a phenotypic distinction.

Accordingly, it is one embodiment of the present invention to alter the activity of the protein encoded by the BP gene normally found in a plant species is altered by introduction of a recombinant version of a non-native BP gene, said recombinant version altered by the addition of one of more DNA sequences that lead to expression of said gene in said plant species, leading to altered activity of the native BP protein. In the present case, altered activity of the BP protein is defined as changes in the inflorescence structure in plants that comprise the non-native BP gene.

Similarly, in a further embodiment of the present invention to alter the expression of a wt BP gene in a plant species by introduction of a recombinant non-native BP gene that alters the activity of the wt BP gene by reduction of the native BP gene expression and reduction of the expression of the protein encoded by the wt BP gene in said plant species.

The identification of this unique genetic activity and specific function allows for novel strategies to manipulate plant morphology or architecture. The sequence can also be used to isolate corresponding related similar or idenitical sequences from other plant species. Related techniques are well understood in the art, for example as provided in Sambrook et al., *Molecular Cloning: A Laboratory Manual*, Cold Spring Harbor Press, Cold Spring Harbor, N.Y. (1989).

The applications of this gene for engineering useful flower/inflorescence architectures in crop and economically important plant species include both the production of more compact flowering structures and conversely methods for the genetic reprogramming of inflorescence structure to produce less compact and more spreading floral structures useful for horticultural applications.

One preferred-application is to develop a bp phenotype in canola crop species (e.g. *Brassica napus, B. rapa*). A compact inflorescence architecture in canola will offer several advantages to this crop that may include reduced shattering and improved overall performance. As one aspect of the present invention, BP-related genes from canola have been isolated and are used to engineer bp-phenotypes.

Similar strategies can be applied to other crop plants by using BP functional homologues from the respective species. Engineering novel and useful architectures using BP or functional homologues is not limited to crop species; potential applications could be extended to horticultural plants to create aesthetically appealing flowers or inflorescences.

Accordingly, in one embodiment of the invention the subject method includes the steps of expressing a BP gene in a plant species comprising the steps of:
  a) Introducing into a plant cell capable of being transformed a genetic construct comprising a first DNA expression cassette that comprises, in addition to the DNA sequences required for transformation and selection in said cells, a DNA sequence derived from a KNAT1 gene, for example, that encodes a peptide having at least 50% homology to the peptide encoded by SEQ ID NO: 5, operably linked to a suitable transcriptional regulatory region and,
  b) recovery of a plant which contains said recombinant DNA, said plant exhibiting altered inflorescence architecture.

The suitable transcriptional regulatory region can be the regulatory region normally associated with the KNAT1 gene or BP coding sequence or a heterologous transcriptional regulatory region capable of expression in the inflorescence.

In another preferred embodiment of the invention the subject method includes a method for modifying the inflorescence architecture of a plant comprising:
  (a) Introducing into a plant cell capable of being transformed and regenerated to a whole plant a genetic construct comprising a first DNA expression cassette that comprises, in addition to the DNA sequences required for transformation and selection in plant cells, a DNA sequence that comprises a polynucleotide region derived from SEQ ID. NO: 5 or 6 encoding a BP gene sequence or part thereof, operably linked to a suitable transcriptional regulatory region and,
  (b) recovery of a plant which contains said recombinant DNA and has altered inflorescence architecture.

The chimeric gene is introduced into a plant cell and a plant cell recovered wherein said gene is integrated into the plant chromosome. The plant cell is induced to regenerate and a whole plant is recovered with altered inflorescence architecture.

The method further relies on the use of transformation to introduce the gene encoding the enzyme into plant cells. Transformation of the plant cell can be accomplished by a variety of different means. Methods that have general utility include *Agrobacterium* based systems, using either binary and cointegrate plasmids of both *A. tumifaciens* and *A. rhyzogenies*. (e.g., U.S. Pat. Nos. 4,940,838, 5,464,763), the biolistic approach (e.g, U.S. Pat. Nos. 4,945,050, 5,015,580, 5,149,655), microinjection, (e.g., U.S. Pat. No. 4,743,548), direct DNA uptake by protoplasts, (e.g., U.S. Pat. Nos. 5,231, 019, 5,453,367) or needle-like whiskers (e.g., U.S. Pat. No. 5,302,523). Any method for the introduction of foreign DNA and/or genetic transformation of a plant cell may be used within the context of the present invention.

It is also apparent to one skilled in the art that the polynucleotide and deduced amino acid sequence of SEQ ID. NO: 5 or 6 can be used to isolate related genes from various other plant species. The similarity or identity of two polypeptide or polynucleotide sequences is determined by comparing sequences. In the art, this is typically accomplished by alignment of the amino acid or nucleotide sequences and observing the strings of residues that match. The identity or similarity of sequences can be calculated by known means including, but not limited to, those described in Computational Molecular Biology, Lesk A. M., ed., Oxford University Press, New York, 1988, Biocomputing: Informatics and Genome Projects, Smith, D. W., ed., Academic Press, New York, 1993, Computer Analysis of Sequence Data. Part 1, Griffin, A. M. and Griffin, H. G., eds., Humana Press, New Jersey, 1994 and other protocols known to those skilled in the art. Moreover, programs to determine relatedness or identity are codified in publicly available programs. One of the most popular programs comprises a suite of BLAST programs, three designed for nucleic acid sequences (BLASTN, BLASTX and TBLASTX), and two designed for protein sequences (BLASTP and TBLASTN) (Coulson, Trends in Biotechnology, 12:76-80, 1994). The BLASTX program is publicly available from NCBI and other sources such as the BLAST Manual, Altschul, S., et al., NCBI NLM NIH Bethesda Md. 20984 provides online help and further literature references for BLAST and related protein analysis methods, and Altschul, S., et al., J. Mol. Biol 215:403-410, 1990.

Within the BP gene two regions are found, the homeodomain and the ELK region. Within the homeodomain region BP shares significant homology with number of other homeodomain proteins (approximately 50 in *Arabidopsis*), and also other plant and animal homeodomain proteins, thus the BP protein represents one of the many homeobox genes.

The isolated polynucleotide can be sequenced and the DNA sequence used to further screen DNA sequence collections to identify related sequences from other species. The DNA sequence collections can comprise EST sequences, genomic sequences or complete cDNA sequences.

In *Arabidopsis* the entire BP coding sequence shares the highest homology with STM which is implicated in meristem maintenance and function(41%), whereas outside of *Arabidopsis*, it shares 53% homology with maize RS1 and 52% with rice OSH15. These genes have been identified by utilizing the conserved domains of plant homeobox genes. Similarly, hybridization can be used to isolate BP functional homologues genes from other species. In the present invention, we have used probes derived from SEQ ID NO: 5 to isolate cDNA sequences homologous to the BP gene of *Arabidopsis*. The present inventors have isolated BP genes from *Brassica napus, B. oleracea* and *B. rapa* using hybridization. These *Brassica* BP genes have been incorporated into plant transformation vectors and have been used to transform plants to obtain plants with altered inflorescence structures.

Accordingly, in one embodiment of the invention the subject method for modifying the inflorescence of a plant comprising the steps of:

a.) Introducing into a plant cell capable of being transformed a genetic construct comprising a first DNA expression cassette that comprises, in addition to the DNA sequences required for transformation and selection in said cells, a DNA sequence that encodes a BP coding sequence encoding a peptide having of at least 50% sequence identity to the peptide encoded by SEQ ID. NO: 5, operably linked to a suitable transcriptional regulatory region and, b.) recovery of a plant which contains said recombinant DNA.

In another embodiment of the present invention, alteration of *Brassica* inflorescence structure is contemplated. Accordingly, the present invention encompasses a method for modifying the inflorescence of a *Brassica* plant comprising the steps of:

a.) Introducing into a *Brassica* plant cell capable of being transformed a genetic construct comprising a first DNA expression cassette that comprises, in addition to the DNA sequences required for transformation and selection in said cells, a DNA sequence that encodes a *Brassica* BP coding sequence encoding a protein of at least 50% sequence identity to the protein sequence encoded by SEQ ID. NO: 5, operably linked to a suitable transcriptional regulatory region and, b.) recovery of a *Brassica* plant which contains said recombinant DNA and exhibits an altered inflorescence.

The use of gene inhibition technologies such as antisense RNA or co-suppression or double stranded RNA interference is within the scope of the present invention. In these approaches, the isolated gene sequence is operably linked to a suitable regulatory element.

Accordingly, in one embodiment of the invention the subject method includes a method to modify the inflorescence of a plant comprising the steps of:

a.) Introducing into a plant cell capable of being transformed a genetic construct comprising a first DNA expression cassette that comprises, in addition to the DNA sequences required for transformation and selection in said cells, a DNA sequence that encodes a BP coding sequence encoding a protein of at least 50% sequence identity to the protein encoded by SEQ ID. NO: 5, at least a portion of said DNA sequence in an antisense orientation relative to the normal presentation to the transcriptional regulatory region, operably linked to a suitable transcriptional regulatory region such that said recombinant DNA construct expresses an antisense RNA or portion thereof of an antisense RNA and, b.) recovery of a plant which contains said recombinant DNA.

It is apparent to the skilled artisan that the polnucleotide encoding the sequence can be in the antisense (for inhibition by antisense RNA) or sense (for inhibition by co-suppression) orientation, relative to the transcriptional regulatory region, or a combination of sense and antisense RNA, to induce double stranded RNA interference (Chuang and Meyerowitz, PNAS 97: 4985-4990, 2000, Smith et al., Nature 407: 319-320, 2000).

A transcriptional regulatory region is often referred to as a promoter region and there are numerous promoters that can be used within the scope of the present invention. In addition, the skilled artisan will readily recognize that the sequence of the inserted recombinant gene must contain regions of sufficient homology to allow for sequence-specific inhibition of gene expression.

Another application for the BP gene is as a visible marker for plant transformation. The advantages of using selection systems that do not include antibiotic/herbicide resistance marker genes for producing transgenic plants are well recognized. Since the bp-1 null mutant represents a phenotype that is clearly visible and easily distinguishable from wild type plants, it is possible to develop transformation vectors based on the BP gene that are devoid of any antibiotic or herbicide selection markers to provide a novel and very efficient alternative to the currently available selection systems. As evidenced by the present invention, the use of the BP gene for complementation of the bp phenotype in *Arabidopsis* demonstrates the it is possible to select for plants that have received a BP gene as a result of transformation with said gene.

It is apparent to the skilled practitioner that any number of methods for the construction of a heterologous genetic construct encoding the protein or portion thereof encoded by SEQ ID. NO: 5 or homologues thereof can be used to alter the architecture of plant wherein said DNA construct has been introduced.

The following examples serve to illustrate the method and in no way limit the utility of the invention.

EXAMPLE 1

Construction and Analysis of *Arabidopsis* bp Mutant Lines

Plant material and genetic analysis. Plants were grown at 22° C. (90% relative humidity) under fluorescent and incandescent light at ~60 µE/m 2/s with 16 h days. The bp mutant seeds were obtained from the *Arabidopsis* Biological Resources Center (ABRC), Ohio State University (stock number CS30; (Koornneef, M., Eden, J. v., Hanhart, C. J., Stam, P., Braaksma, F. J. & Feenstra, W. J. (1983) *J. Hered.* 74, 265-272.)). This allele was designated bp-1. A second bp allele (bp-2) was isolated from promoter-tagged *Arabidopsis* lines in RLD background. This allele was introgressed into Ler and backcrossed five times with wild type (wt). bp-2 was introduced into Columbia (Col) wt background from Ler and backcrossed three times.

Histology. Plant samples were fixed for 24 h at room temperature in FAA and paraffin embedded as described (Johansen, D. A. (1940) *Plant microtechnique* (McGraw-Hill Book Co., New York)). Serial sections were taken at 8 µm on a rotary microtome, attached to glass slides with Mayer's egg albumin (Sigma) solution, and dried on a warming tray (42° C.). Sections were stained after removal of the embedding medium in toluidine blue O. The sections were observed under a Leitz (Wetzlar) microscope and images were captured using, Optronics DEI 750 digital microscope camera.

Scanning electron microscopy. For scanning electron microscopy (SEM) the samples were fixed in 3% glutaraldehyde and processed as described (Venglat, S. P. & Sawhney, V. K. (1996) *Planta* 1968, 480-487.). Samples were mounted on aluminum stubs and coated with gold in an Edwards S150B sputter-coater. Observations were made with a Phillips SEM 505 scanning electron microscope at 30 kV and recorded using Polaroid type 665 P/N. Images were scanned and enhanced using Adobe Photoshop 4.0.

Architectural Changes in the infloresence of bp mutants. In all bp plants the earliest signs of alteration of the inflorescence are evident at the time of bolting, with more compactly arranged floral buds at the apex; the effects were more pronounced when the first few co-florescence internodes from the rosette leaves started elongating. At maturity, bp plants display a marked reduction in overall height, primarily as a result of shortened internodes; moreover, the floral internodes were affected to a greater extent than the co-florescence internodes (FIGS. 1, 2). Additionally, bending at nodes was observed and this phenotype was more severe in bp-1 than bp-2 plants. bp-2 in RLD (the original isolate) and Col backgrounds showed similar patterns, although the reduction in internodal lengths was less than observed in Ler background. bp affects cell division and cell differentiation in the internodes of the inflorescence. SEM analysis showed that the floral buds began pointing downwards quite early in their development and that the internodal elongation is significantly reduced. The peduncle surface showed stripes consisting of cell files (~5 cells in width) with changes in epidermal cell differentiation (defined by alterations in bp lines in cell size, shape, and/or cell type (stomata) in relation to similar regions in wt) associated with regions below the nodes (FIG. 3). Cross sections through internodes in bp indicated that the overall radial pattern, in terms of tissue types, was very similar to the wt (FIG. 3). However, small sectors with changes in epidermal cell differentiation are observed, and these corresponded to the stripes of differentiation-altered cells observed by SEM. Furthermore, the cortical cells below these sectors were had changes in differentiation (indicated by a lack of chloroplasts), and the cells were relatively larger with less intercellular space. Longitudinal sections through the nodes showed sectors of epidermal and sub-epidermal changes. As the cell number per unit area along the main axis of the peduncle in BP was comparable to the wt, the reduced internodal length was interpreted to be a result of fewer cell divisions.

BP causes changes in inflorescence development. Pedicels in bp plants at all the floral nodes showed a drastic reduction in length compared with wt (FIG. 2), in addition to downward-pointing siliques (FIG. 1). The degree of the latter phenotype conferred by bp-2 varied in different backgrounds from downward-pointing (Ler) to less acute bending in RLD and Col backgrounds. Since very little is known about pedicel development in any plant species, including *Arabidopsis*, we determined its ontogeny in Ler wt compared with bp. Pedicel initiation was first observed around stage 3 flowers, followed by elaboration of the pedicel with coordinated development on both the abaxial and adaxial sides, and along the proximo-distal axis. The first signs of epidermal differentiation. (defined by characteristic changes in cell shape and the appearance of stomata) were observed on the abaxial side at stage 9, and this was closely followed by differentiation on the adaxial side in subsequent stages. By stage 12 epidermal cell differentiation was completed with no apparent differences observed between the abaxial and adaxial sides in the wt (FIG. 4). In bp, no detectable differences from wt were observed up to stage 3. However, the pedicel differentiation and elaboration processes lagged behind the wt and the first sign of epidermal cell differentiation was observed only at stage 12, and this was restricted to the adaxial surface; no corresponding differentiation was observed on the abaxial side, even by the mature stage (FIG. 4). Anatomical analysis showed that while the major part of the pedicel in bp contained defects in the differentiation of abaxial-side epidermal cells and cortical cells (FIG. 4), the distal region including the receptacle was more strongly affected with a significantly reduced pith region, cell size and differentiation, and radial growth (FIG. 4). Longitudinal sections through the pedicels also showed that the cells in the epidermal layer and cortical tissues on the abaxial side were less elongated (FIG. 3). Furthermore, there were fewer cells in the proximo-distal axis of the pedicel, indicative of fewer cell divisions. Although there were no apparent defects observed in the sepals, petals, and stamens, the carpels showed detectable differences in bp. Notably, there was reduced radial growth of the style (FIG. 5), although there was variability observed between plants regarding this phenotype. The epidermal and cortical cells of the style, especially in the lateral axis, were defective in differentiation and elongation, and as a consequence the arrangement of stigmatic papillae was significantly altered (FIG. 5). These observations support a functional role for BP in maintaining the normal growth and radial symmetry of the style. The developmental and anatomical studies suggested that the defects in bp were only associated with the peduncle and parts of the flower but not with the leaves.

EXAMPLE 2

Isolation of the KNAT1 Coding Sequence

To isolate the KNAT1 coding sequence, cDNA cloning was used. Reverse transcription was carried out using 3-5 µm of total RNA from stem tissue of wt (Col, Ler, RLD) and bp plants and Superscript II RT (Life Technologies). To amplify the KNAT1 open reading frame (ORF), 1 µl of cDNA was used for PCR with primers

```
Seq ID NO: 1
954 DNA SEQ
5' cgggatccatggaagaataccagcatgac 3'
and

SEQ Id NO: 2
955 DNA SEQ
5' cgggatccggtacctggatgtcttatggaccgag 3'
``` and Pfu polymerase (1 U). Amplification of the cytosolic glyceraldehyde-3-phosphate dehydrogenase (gapc) cDNA (Shih, M.-C., Heinrich, P. C. & Goodman, H. M. (1991) *Gene* 104, 133-138.) from the same cDNA pools was performed under the same conditions

```
Seq ID NO: 3
DNA SEQ gapC-UP
5' accactaactgccttgctc 3'
and

SEQ ID NO: 4
DNA SEQ gapC-DN
5' caatttcacaaacttgtcgctc 3'
```

KNAT1-encoding PCR products were cloned and sequenced by primer walking using an ABI 377 DNA sequencer. The sequence of the wt KNAT1 gene is shown in Seq ID NO: 5.

EXAMPLE 3

Expression of BP Genes

Based on the discovery that BP represents the previously described KNAT1 gene, probes for KNAT1 were generated as described above and used to analyzed BP transcript levels in col wt and Ler wt by northern blots and by the more sensitive RT-PCR. Results from these experiments showed 2-4 times higher transcript levels in col wt ecotype (data not shown).

EXAMPLE 4

Isolation of BP Genomic Regions

The BP appears to be expressed predominantly in stem and pedicel tissues in wt plants. To clone BP, a region between DET1 and the centromere on chromosome 4 was chosen, based on genetic maps compiled from several data sets (Pepper, A., Delaney, T., Washburn, T., Poole, D. & Chory, J. (1994) Cell 78.)). To produce probes reflecting the anticipated expression pattern of BP, polyA+RNA was isolated from both stem/pedicel and leaf tissues in Col wt plants and a Suppression subtractive hybridization (SSH) was performed using leaf cDNA as driver. Total RNA was harvested from stem/pedicel and leaf tissues of Col wt using Trizol Reagent (Life Technologies). Poly A+RNA was isolated using mRNA spin columns (Clontech). cDNA synthesis was carried out using a cDNA synthesis kit (Life Technologies). A total of 2 µg each of leaf cDNA (driver) and stem/pedicel cDNA (tester) was digested with HaeIII (New England Biolabs) and used for suppression subtractive hybridization as described (Diatchenko, L, et al. (1996) Proc. Natl. Acad. Sci. USA 93, 6025-6030.). The subtracted mix was 32 P-labeled using a RediPrime kit (AP Biotech) and used to screen Bacterial Artificial Chromosome (BAC) DNA preparations as described below.

BAC clones from chromosome 4 were obtained from the ABRC. DNA was prepared from 10-ml cultures of BACs T17A2, T13D4, F9M13, T12G3, T28D5, T15F16, T3F12, T32A17, T3H13, F23J3, T8A17, T30A10, T15G18, T25P22, and T24H23 using an alkaline lysis miniprep method (Ausubel, F. M., Brent, R., Kingston, R. E., Moore, D. D., Seidman, J. G., Smit, J. A. & Struhl, K. (1995), (John Wiley and Sons, Inc., New York).). BAC DNA was digested with BamHI, EcoRI, or HindIII (Life Technologies), fractionated on a 0.8% agarose gel, then blotted to a Zeta Probe membrane (BioRad) using standard procedures as described (Ausubel, et al, ibid.) The blot was probed with the pooled subtracted mix representing cDNAs expressed in stem/pedicel tissue, prepared as described above. Genomic DNA (5 µm) isolated from leaves (Dellaporta, S. (1994) in *The Maize Handbook*, eds. Freeling, M. & Walbot, V. (Springer-Verlag, New York), pp. 522-525) of wt and bp plants was digested using 30 U BamHI or EcoRI (Life Technologies) at 37° C. for 8 hours, processed as above, and probed with the 32 P-labeled KNAT1 RT-PCR product from Col wt. Hybridization proceeded for 3 h (BAC screen) or overnight (genomic Southern blot) at 65° C. in QuickHyb hybridization solution (Stratagene); the most stringent wash was in 0.1×SSC/0.1% SDS at 65° C. The blots were exposed to X-OMAT AR film (Kodak) overnight at −70° C. PCR, RT-PCR, and DNA sequencing.

The pooled subtracted products were then used as a probe in a Southern blot with 15 BACs as targets spanning a region of approximately 1.5 Mb on chromosome 4 between DET1 and the centromere. A BamHI fragment of about 20 kb from BAC F9M13 was the only band that showed any hybridization to the subtracted probe. BAC F9M13 (GenBank AC006267) contains a single gene on this 20-kb BamHI fragment within a region rich in repeats. Subsequent fingerprinting of F9M13 with this probe confirmed that the probe detected the previously reported homeobox gene KNAT1.

EXAMPLE 5

Determination of BP Gene Coding Sequence in bp Mutant and Wild Type Lines

It was found that the bp-1 mutant represented a deletion of the BP gene. To identify the molecular basis for the bp-2 mutant phenotype, BP-encoding RT-PCR products from duplicate reverse transcription reactions using L. er (wt), RLD (wt), bp-2 (col), bp-2 (Ler), and bp-2 (RLD) were then cloned and their sequences determined. It was found that the bp-2 lines contained an altered protein coding sequence which has a C-T transition corresponding to position 535 of the col (wt) ORF. This is shown in SEQ ID NO: 6, the bp-2 coding region. This point mutation changed codon 179 from cag to tag, thereby introducing a stop codon and resulting in a truncated predicted protein sequence shown in SEQ ID NO: 7.

This sequence analysis further demonstrated that in wt Ler and RLD the BP ORFs encoded predicted proteins of 400 aa, compared with a predicted protein of 398 aa for col wt.

EXAMPLE 6

Complementation of bp Mutant Lines

In order to demonstrate the function of the KNAT1 gene in the bp phenotype, plants exhibiting a bp phenotype were transformed with a wild-type KNAT1 gene under the control of the native BP (KNAT1) promoter. Two different complementation constructs were prepared. The structure of the vectors used for complementation of the bp phenotype in *Arabidopsis thaliana* is as follows:

The backbone for both vectors was pRD400 (Datla, R. S. S., J. K. Hammerlindl, B. Panchuk, L. E. Pelcher, and W. Keller. 1992. Modified binary plant transformation vectors with the wild-type gene encoding NPTII. Gene 122:383-384). This vector was used to derive two plant transformation vectors. In both constructs, the BamHI sites at the junction of the promoter and ORF were introduced to facilitate assembly of the constructs. B, BamHI; Bg, BglII, K, KpnI. Parentheses indicate sites destroyed by ligation.

Construct A. Referred to as pRD400-951/955, consisting of the KNAT1 cDNA (SEQ ID NO: 5) cloned downstream of the putative KNAT1 promoter as shown in FIG. 8. The KNAT1 promoter was isolated by PCR using the following primers:

```
SEQ ID NO: 8
DNA SEQ 951
5' cccaagcttagatctttcggtctagtgcagtgatg 3'
and

Sequence ID NO: 9
DNA SEQ 952
5' ccggatcccagatgagtaaagatttg 3'
``` for amplification of the putative KNAT1 promoter; 1536 bp product corresponding to the region immediately upstream of the KNAT1 start codon. Amplification conditions for all primers using genomic DNA as template were as follows: 94° C., 2 min followed by 30 cycles of 94° C., 15 sec; 55° C., 30 sec; and 72° C., 4-6 min. A final extension of 10 min at 72° C. was performed. All amplifications from genomic DNA used Pfu polymerase (Stratagene) (2.5 U) and a PTC-200 thermal cycler (MJ Research).

Construct B. Referred to as pRD400-951/956, consisting of the putative KNAT1 promoter and the KNAT1-encoding ORF amplified from genomic DNA. To amplify the KNAT1 coding region, two primers were used, Seq ID NO: 1 (as described in example 2), and

```
SEQ ID NO: 10
DNA SEQ 956
5' gaagatctgtcgacgccttgtgcttgattgagactcca 3'
``` for amplification of the protein coding region and terminator from genomic DNA; 3347-bp product from the KNAT1 start codon to a point 705 bp downstream of the stop codon, including the putative transcriptional terminator.

*Agrobacterium tumefaciens* GV3101 containing these recombinant constructs were used to transform bp-2 (Ler) plants by vacuum infiltration (Bechtold, N., Ellis, J. & Pelletier, G. (1993) *C.R. Acad. Sci. Ser. III* 316, 1194-1199). Transformation of bp-2 (Ler) with the genomic clone of KNAT1 resulted in 20 transformants; 4 were completely rescued to wt, while the others were partially rescued. Southern analysis confirmed that these complemented lines contained the KNAT1 wt transgene. Further analysis of two of these single transgene copy lines showed a 3:1 (wt:bp) segregation pattern in the T2 generation, providing genetic confirmation of complementation. Complementation of BP with KNAT1 cDNA was also observed.

EXAMPLE 7

Overexpression of the *Arabidopsis* BP Gene

In this example, the native *Arabidopsis* BP gene (wt KNAT1) was used for over expression. The BP gene coding region (SEQ ID. NO: 5) was used to make an over expression construct with enhanced 35S promoter referred to as pRD400-35S::AtbpS, consisting of the *A. thaliana* BP ORF under the control of the 35S promoter assembled using routine methods. This vector is shown in FIG. 10. The vector was used to transform *Arabidopsis* as above.

EXAMPLE 8

Expression of the *Arabidopsis* BP Gene in Heterologos Species

The vector pRD400-35S::AtBPS was used to transform *B. napus*. The vector was inserted into *Agrobacterium* stain MP90 by standard triparental mating followed by *Agrobacterium*-mediated transformation of *Brassica*. Transformation was essentially carried out as described by Moloney et al., *Plant Cell Reports* 8:238-242, 1989.

EXAMPLE 9

Construction of Antisense *Arabidopsis* BP Genes

The BP coding region was used to construct an antisense construct under its own promoter (1.5 kb) and also the 35S promoter. For expression of antisense RNA under the 35S promoter, the vector pRD400-35S::AtBPA/S, consisting of the *A. thaliana* bp ORF in an antisense orientation under the control of the 35S promoter was constructed and is shown in FIG. 11.

For expression of antisense RNA under the KNAT1 promoter, the vector pRD400-951/952::AtbpA/S, consisting of the *A. thaliana* bp cDNA (nucleotides 481-1227) in an antisense orientation under the control of the *A. thaliana* KNAT1 promoter was constructed and is Shown in FIG. 12.

Terms used: Nos Ter, Nos terminator. B, BamHI; Bg, BglII, K, KpnI; H, HindIII, S, SstI.

EXAMPLE 10

Expression of an Altered *Arabidopsis* BP Gene

In this example, the protein encoded by SEQ ID NO: 6 was expressed under its own promoter (1.5 kb) and also the 35S promoter.

For expression of the altered BP gene under the 35S promoter, the vector pRD400-35S::Atbp-2, consisting of the *A. thaliana* bp-2 ORF under the control of the 35S promoter is constructed using the same procedures as for the wild-type coding sequence and is shown in FIG. 12.

For expression of the altered BP gene under the KNAT1 promoter, the vector pRD400-951/952::Atbp-2, consisting of the *A. thaliana* bp-2 cDNA (nucleotides 481-1227) in an antisense orientation under the control of the *A. thaliana* KVAT1 promoter is constructed as above and is shown in FIG. 13.

EXAMPLE 11

Isolation of BP Related Coding Sequences from other Species: *B. napus*

The *A. thaliana* KNAT1 (BP) cDNA isolated in example 2 was used to screen a cDNA library prepared from stem tissues of *B. napus*. A total of 200,000 pfu were initially screened under moderate stringency hybridization conditions (hybridization solution contained 30% formamide/5×SSC/5× Denhardt's solution/0.5% SDS/50 μm/ml salmon sperm DNA at 42° C., with final washes in 0.1×SSC/0.1% SDS at 55° C.). 13 plaques were purified from these primary screens; these were excised from their phagemid hosts and sequenced.

BLAST analysis showed that the clones fell into 3 groups: nonspecific clones (discarded); homeobox gene-like sequences that were not likely orthologs of *A. thaliana* Knat1;

and apparent Knat1 orthologs. The latter group was represented the most frequent and consisted of both full-length and 5' truncated clones. The complete sequence on both strands was determined for the longest cDNA isolated from these screens (1515 bp), which was designated the name Bnbp.

This cDNA contained an ORF of 1158 bp with 73 nucleotides of 5' untranslated region (UTR) and 284 nucleotides of 3' UTR and is shown in SEQ ID NO: 11. The predicted protein encoded by this cDNA was 385 amino acids in length and showed 86.3% similarity (PAM250 residue weight table) to A. thaliana bp.

```
PCR primers
SEQ ID NO: 12:
5'-cgggatccatggaagaatatcaacatgaa-3'

SEQ ID NO: 13:
5'-cgggatccggtaccttatggtccaagacgat-3'
``` were designed to amplify the ORF from this cDNA with ends modified with BamHI/NcoI (5' end) and BamHI/KpnI (3' end) to facilitate its insertion into the expression constructs described above. The Bnbp ORF was amplified from the cDNA isolated from the library screens with Pfu polymerase (Stratagene) and cloned into a standard PCR product cloning vector pCR2.1; Invitrogen).

EXAMPLE 12

Isolation of BP Related Coding Sequences from other Species: *B. rapa, B. oleracea*

The PCR primers that were designed to amplify the Bnbp ORF were used to isolate bp orthologs from species closely related to *B. napus*. Total RNA was extracted from *B. rapa* and *B. oleracea* (kale) hypocotyls harvested 6 days after germination and used as a template for first strand cDNA synthesis with Superscript II reverse transcriptase (Life Technologies). This cDNA was then used as a PCR template to amplify bp-like cDNAs from these species. PCR products were cloned into a standard vector (pCR2.1) and their sequences determined by primer walking. The sequences are shown in Seq ID Nos. 14 and 15.

EXAMPLE 13

Isolation of BP Related Genes from other Species: *B. rapa, B. oleracea*

Isolation of genomic clones encoding BP from *B. napus, B. rapa*, and *B. oleracea*. Using the sequences of the bp cDNAs determined as described above, PCR primers were designed to amplify the genomic copies (including introns) of the BP genes from each species (*B. napus, B. rapa, B. oleracea*). The primers used were:

Seq ID NO: 16: PCR Primer used to Amplify *B. napus* BP from Genomic DNA

```
5'-ataacaccaccaccaacaac-3'
```

Seq ID NO: 17: PCR Primer used to Amplify *B. napus* BP from Genomic DNA

```
5'-actaggaagtctcaaacccc-3'
```

Seq ID NO: 18: PCR Primer used to Amplify *B. rapa, B. oleracea* BP from Genomic DNA

```
5'-tcaacatgaaagcagatccac-3'
```

Seq ID NO: 19: PCR Primer used to Amplify *B. rapa, B. oleracea* BP from Genomic DNA

```
5'-aacgagagaggcaacaaaag-3'
```

The PCR products (approximately 3.8 kb for each species) were cloned into pCR2.1 and their sequences were determined by primer walking.

The sequence of the *B. napus* bp genomic region isolated using primers as described in Seq ID nos. 16 and 17 is shown in SEQ ID NO: 20

The sequence analysis revealed that the *B. napus* BP coding region, like that of *A. thaliana* BP, is interrupted by 4 introns. The positions and relative lengths of the introns were all similar to the *A. thaliana* BP gene.

EXAMPLE 14

Isolation of BP Promoter Regions from *B. napus*

Isolation of sequences upstream of *B. napus* BP, including the probable promoter. The sequence of the BP-encoding cDNA from *B. napus* was used to design primers to isolate 5' regions of the bp gene. Primers used were:

SEQ ID NO: 21: PCR Primer used to Amplify the Region Upstream of the bp gene from *B. napus*

```
5'-catgatcggatcggaagcaattctcagtcg-3'
```

SEQ ID NO: 22: PCR Primer used to Amplify the Region Upstream of the bp gene from *B. napus*

```
5'-aaaagttgagagagaaagagagagagagag-3'
``` to isolate the putative promoter-containing region from genomic DNA. For this purpose, a Genome Walker kit (Clontech) was used. Following the standard protocols in the kit, two fragments (840 and 950 bp) were isolated that represent the likely promoters of the two BP genes of *B. napus*. The sequences are presented in SEQ ID Nos. 23 and 24.

EXAMPLE 15

Construction of a Vector Comprising the *Brassica* BP Gene Under the Control of an *Arabidopsis* Promoter The map of the vector of pRb400-9511/952'::BnBPS, consisting of the *B. napus* BP ORE (SEQ ID. NO: 11) under the control of the *A. thaliana* KNAT1 promoter constructed using standard techniques is shown in FIG. 14. The vector was used to transform *Arabidopsis* and *Brassica napus* as described.

EXAMPLE 16

Construction of a Vector Comprising the *Brassica* BP Gene Under the Control of a Constitutive Promoter The vector map of pRD400-35S::BnBPS, consisting of the *B. napus* BP ORF (Seq ID NO: 11) under the control of an optimized cauliflower mosaic virus (CaMV) 35S promoter (Datla, R. S. S., F. Bekkaoui, J. K. Hammerlindl, G. Pilate, D. I. Dunstan, and W. L. Crosby. 1993. Improved high-level constitutive foreign gene expression in plants using an AMV RNA4 untranslated leader sequence. Plant Sci. 94:139-149) is shown in FIG. 15. The vector was assembled using well-known techniques as described. The vector was used to transform *Arabidopsis* and *Brassica napus* as described herein.

EXAMPLE 17

Construction of a Vector Comprising a *Brassica* Antisense BP Gene Under the Control of a Constitutive Promoter The vector map pRD400-35S::BnbpA/S, consisting of the *B. napus* BP ORF in an antisense orientation under the control of the 35S promoter is shown in FIG. 16. The vector was assembled using well-known techniques as described. The vector was used to transform *Arabidopsis* and *Brassica napus* as described herein.

Sequence Listing Free Text
SEQ ID NO: 1 954 DNA SEQ—PCR primer
SEQ ID NO: 2 955 DNA SEQ—PCR primer
SEQ ID NO: 3 DNA SEQ gapC-UP—PCR primer
SEQ ID NO: 4 DNA SEQ gapC-DN
SEQ ID NO: 8 DNA SEQ 951—PCR primer
SEQ ID NO: 9 DNA SEQ 952—PCR primer
SEQ ID NO: 10 DNA SEQ 956—PCR primer
SEQ ID NO: 12 PCR primer
SEQ ID NO: 13 PCR primier
SEQ ID NO: 16 PCR primer
SEQ ID NO: 17 PCR primer
SEQ ID NO: 18 PCR primer
SEQ ID NO: 19 PCR primer
SEQ ID NO: 21 PCR primer
SEQ ID NO: 22 PCR primer

```
Sequence ID listing
Seq ID NO: 1 954 DNA SEQ (Synthetic DNA)
5' cgggatccatggaagaataccagcatgac 3'

SEQ Id NO: 2 955 DNA SEQ (Synthetic DNA)
5' cgggatccggtacctggatgtcttatggaccgag 3'

Seq ID NO: 3 DNA SEQ gapC-UP (Synthetic DNA)
5' accactaactgccttgctc 3'

SEQ ID NO: 4 DNA SEQ gapC-DN (Synthetic DNA)
5' caatttcacaaacttgtcgctc 3'

Seq ID NO: 5 KNAT 1 gene (cDNA Sequence)
5'cgggatccatggaagaataccagcatgacaacagcaccactcctcaaa gagtaagtttcttgtactctccaatctcttcttccaacaaaaacgataac acaagtgataccaacaacaacaacaataataatagtagcaattatgg tcctggttacaataatactaacaacaacaatcatcaccaccaacacatgt tgtttccacatatgagctctcttctccctcaaacaaccgagaattgcttc cgatctgatcatgatcaacccaacaacaacaacaacccatctgttaaatc tgaagctagctcctcaagaatcaatcattactccatgttaatgagagcca tccacaatactcaagaagctaacaacaacaacaatgacaacgtaagcgat gttgaagccatgaaggctaaaatcattgctcatcctcactactctaccct cctacaagcttacttggactgccaaaagattggagctccacctgatgtgg ttgatagaattacggcggcacggcaagactttgaggctcgacaacagcgg tcaacaccgtctgtctctgcctcctctagagacccggagttagatcaatt catggaagcatactgtgacatgttggttaaatatcgtgaggagctaacaa ggcccattcaggaagcaatggagtttatacgtcgtattgaatctcagctt agcatgttgtgtcagagtcccattcacatcctcaacaatcctgatgggaa gagtgacaatatgggatcatcagacgaagaacaagagaataacagcggag gggaaacagaattaccggaaatagacccgagggccgaagatcgggaactc aagaaccatttgctgaagaagtatagtggatacttaagcagtttgaagca agaactatccaagaagaaaaagaaaggtaaacttcctaaagaagcacggc agaagcttctcacgtggtgggagttgcattacaagtggccatatccttct gagtcagagaaggtagcgttggcggaatcaacgggggttagatcagaaaca aatcaacaattggttcataaaccaaagaaagcgtcactggaaaccatctg aagacatgcagttcatggtgatggatggtctgcagcacccgcaccacgca gctctgtacatggatggtcattacatgggtgatggaccttatcgtctcgg tccataagacatccaggtaccggatcccg 3'

SEQ ID NO: 6, the
bp-2 coding region (cDNA Sequence)
5'cgggatccatggaagaataccagcatgacaacagctccactcctcaaa gagaagtttcttgtactctccaatctcttcttccaacaaaaacgataaca caagtgataccaacaacaacaacaacaataataatagtagcaattatggt cctggttacaataatactaacaacaacaatcatcaccaacacatgtt gtttccacatatgagctctcttctccctcaaacaaccgagaattgcttcc gatccgatcatgatcaacccaacaacaacccatctgttaaatctgaagct agctcctcaagaatcaatcattactccatgttaatgagagccatccacaa tactcaagaagctaacaacaacaacaatgataacgtaagcgatgttgaag ccatgaaggctaaaatcattgctcatcctcactactctaccctcctacaa gcttacttggactgccaaaagattggagctccacctgacgtggttgatag aattacggcggcacggcaagactttgaggctcgacaatagcggtcaacac cgtctgtctctgcctcctctagagacccggagttagatcaattcatggaa gcatactgtgacatgttggttaaatatcgtgaggagctaacaaggcccat tcaggaagcaatggagtttatacgtcgtattgaatctcagcttagcatgt tgtgtcagagtcccattcacatcctcaacaatcctgatgggaagagtgac aatatgggatcatcagacgaagaacaagagaataacagcggaggggaaac agaattaccggaaatagacccgagggccgaagatcgggaactcaagaacc atttgctgaagaagtatagtggatacttaagcagtttgaagcaagaacta tccaagaagaaaaagaaaggtaaacttcctaaagaagcacggcagaagct
```

-continued tctcacgtggtgggagttgcattacaagtggccatatccttctgagtcag agaaggtagcgttggcggaatcaacggggttagatcagaaacaaatcaac aattggttcataaaccaaagaaagcgtcactggaaaccatctgaagacat gcagttcatggtgatggatggtctgcagcaccgcaccacgcagctctgt acatggatggtcattacatgggtgatggacctatcgtctcggtccataa gacatccaggtaccggatcccg 3'

SEQ ID NO: 7 predicted
bp-2 protein (Protein Sequence).
MEEYQHDNSSTPQRVSFLYSPISSSNKNDNTSDTNNNNNNNNSSNYGPGY

NNTNNNNHHHQHMLFPHMSSLLPQTTENCFRSDHDQPNNNPSVKSEASSS

RINHYSMLMRAIHNTQEANNNNNDNVSDVEAMKAKIIAHPHYSTLLQAYL

DCQKIGAPPDVVDRITAARQDFEARQ*

SEQ ID NO: 8 DNA SEQ 951 (Synthetic DNA)
5'cccaagcttagatctttcggtctagtgcagtgatg 3'

Sequence ID NO: 9 DNA SEQ 952 (Synthetic DNA)
5' ccggatcccagatgagtaaagatttg 3'

SEQ ID NO: 10 DNA SEQ 956 (Synthetic DNA)
5' gaagatctgtcgacgccttgtgcttgattgagactcca 3'

SEQ ID NO: 11:
B. napus bp gene(BnBP) (cDNA Sequence)
5'ggcacgagcacattagttttttatattctctctctctctctctcttc tctctcaacttttattcatctgggtatggaagaatatcaacatgaaagca gatccactcctcatagagtaagtttcttgtactctccaatctcttcttcc aacaaaatgataacaccaccaccaacaacaataataccaattatggttc tggttacaataatactaataacaatcatcaacaacacatgttgttcc cacatatgagctctcttcttcctcaaacgactgagaattgcttccgatcc gatcatgatcagcctaccaacgcatctgtttaaatcagaagcaagctcctc aagaatcaatcactactctatgttgatgaaagccatccacaatactcaag aaactaacaacaacaatgatacggaatccatgaaagctaagatcatc gctcatccccactactccaccctcctacacgcctacttggactgccagaa gattggagcaccacctgaggtggtcgataaaattacggcggcaagacaag agttcgaggcgaggcagcagcggccaacagcgtccgtaactgcgctgtct agagacccggaattggatcaattcatggaagcatactgtgatatgctggt taaatatcgagaggagctaacacgcccattgaagaagcaatggagtata tacgtcgtattgaatctcaaattagcatgttgtgtcagggtcccattcac atcctcaacaatcctgatgggaaagtgaaggaatagaatcatcagacga agagcaagataataacaacagtggaggggaagcagaattaccggaaatag acccgagggcggaagatcgggaactcaagaatcacttgctgaagaagtac agtggatacttgagcagtctaaagcaagaactgtccaagaaaaaaagaa aggtaaacttcccaaagaagcaaggcagaagcttctcacgtggtgggaat tgcattacaagtggccgtatccttctgaatcagagaaggtggcgttggcg gaatcaacggggttagatcagaaacagatcaacaattggttcataaacca agaaaacgtcactggaaaccgtccgaggacatgcagttcatggtgatgg atggtctacagcacccgcaccacgcagctctatacatggatggtcattac atgggcgatggtccttatcgtcttggaccataagagaccacatgcagata tccagaagggttagccatataataacaaccttttgttgcctctctcgttt acagttcatgatttcaactttccttcacaagtttgctacctatagcttta ttttcttacccgtatttaatgtcttatatcgttcaaggggtttgagactt cctagtcattttcacttttattttgtatttttcataatgttttatttat aatatgtgttctaataatgtgtgaaaagagatgttttatgaattttaaa aaaaaaaaaaaaaaaa 3'

SEQ ID NO: 12: PCR Primer (Synthetic DNA)
5'-cgggatccatggaagaatatcaacatgaa-3'

SEQ ID NO: 13: PCR Primer (Synthetic DNA)
5'-cgggatccggtaccttatggtccaagacgat-3'

Seq ID NO: 14: B. rapa bp gene (cDNA Sequence)
5'cgggatccatggaagaatatcaacatgaaagcagatccactcctcata gagtaagtttcttgtactctccaatctcttcttccaacaaaaatgataac accaccaccaacaacaataataccaattatggttctggttacaataatac taataacaataatcatcaacaacacatgttgttcccacatatgagctctc ttcttcctcaaacgactgagaattgcttccgatccgatcatgatcagcca ccaacgcatctgttaaatcagaagcaagctcctcaagaatcaatcacta ctctatgttgatgaaagccatccacaatactcaagaagctaacaacaaca acaacaacaaygatatggaatccatgaaagctaagatcatcgctcatcct cactactccaccctcctacacgcctacttggactgccagaagattggagc accacctgaagtggttgataaaattacggcggcaagacaagaattcgagg cgaggcagcagcggccaacagcgtccgtaactgcgctgtctagagacccc gaattggatcaattcatggaagcatactgtgatatgctggttaaatatcg agaggagctaacacgcccattgaagaagcaatggagtatatacgtcgta ttgaatctcagattagcatgttgtgtcagggtcccattcacatcctcaac aatcctgatgggaaagtgaaggaatggaatcatcagacgaagagcaaga taataacaacagtggaggggaagcagaattaccggaaatagacccgaggg cggaagatcgggaactcaagaatcacttgctgaagaaatacagtggatac ttgagcagtctaaagcaagaactgtccaagaaaaaaagaaaggtaaact tcccaaagaagcaaggcagaagcttctcacgtggtgggaattgcattaca agtggccgtatccttctgaatcagagaaggtggcgttggcggaatcaacg gggttagatcagaaacagatcaacaattggttcataaaccaaagaaacg tcactggaaaccgtccgargacatgcagttcatggtgatggatggtctac agcacccgcaccacgcagctctatacatggatggtcattacatgggcgat ggcccttatcgtcttggaccataaggtaccggatcccg3'

SEQ ID NO: 15: B. Oleracea bp gene (cDNA Sequence)
5'cgggatccatggaagaatatcaacatgaaagcagatccactcctcata gagtaagtttcttgtactctccaatctcttcttccaacaaaaatgataac accaccaccaacaacaataataccaattatggttctggttacaataatac taataacaataatcatcaacaacacatgttgttcccacatatgagctctc -continued ttcttcctcaaacgactgagaattgcttccgatccgatcatgatcagcct
accaacgcatctgttaaatcagaagcaagctcctcaagaatcaatcacta
ctctatgttgatgaaagccatccacaatactcaagaaactaacaacaaca
acaatgatacggaatccatgaaagctaagatcatcgctcatccccactac
tccaccctcctacacgcctacttggactgccagaagattggagcaccacc
tgaggtggtcgataaaattacggcggcaagacaagagttcgaggcgaggc
agcagcggccaacagcgtccgtaactgcgctgtctagagacccggaattg
gatcaattcatggaagcatactgtgatatgctggttaaatatcgagagga
gctaacacggcccattgaagaagcaatggagtatatacgtcgtattgaat
ctcaaattagcatgttgtgtcagggtcccattcacatcctcaacaatcct
gatgggaaaagtgaaggaatagaatcatcagacgaagagcaagataataa
caacagtggaggggaagcagaattaccggaaatagacccgagggcggaag
atcgggaactcaagaatcacttgctgaagaagtacagtggatacttgagc
agtctaagcaagaactgtccaagaaaaaaagaaaggtaaacttcccaaa
gaagcaaggcagaagcttctcacgtggtgggaattgcattacaagtggcc
gtatccttctgaatcagagaaggtggcgttggcggaatcaacggggttag
atcaaaaacagatcaacaattggttcataaaccaaagaaaacgtcactgg
aaaccgtccgaggacatgcagttcatggngatggatggtctacagcaccc
gcaccacgcagctctatacatggatggtcattacatgggcgatggtcctt
atcgtcttggaccataaggtaccggatcccg3'

Seq ID NO: 16: PCR Primer (Synthetic DNA)
5'-ataacaccaccaccaacaac-3'

Seq ID NO: 17: PCR Primer (Synthetic DNA)
5'-actaggaagtctcaaacccc-3'

Seq ID NO: 18: PCR Primer (Synthetic DNA)
5'-tcaacatgaaagcagatccac-3'

Seq ID NO: 19: PCR Primer (Synthetic DNA)
5'-aacgagagaggcaacaaaag-3'

Seq ID NO: 20:
B. napus BP genomic fragment (Genomic DNA)
5'ataacaccaccaccaacaacaataataccaattatggttctggttaca
ataatactaataacaataatcatcaacaacacatgttgttcccacatatg
agctctcttcttcctcaaacgactgagaattgcttccgatccgatcatga
tcagccaaccaacgcatctgttaaatcagaagcaagctcctcaagaatca
atcactactctatgttgatgaaagccatccacaatactcaagaagctaac
aacaacaacaacaatgatatggaatccatgaaagctaagatcatcgc
tcatccgcactactccaccctcctacacgcctacttggactgccagaagg
ttatatagatttagcactggatttcgttttattttgttgtagtaatata
taaaataccactcttgtttgtttaaattaacgagatgatatgcgtaaata
tgttcacggggttgcatatacagattggagcaccacctgaagtggttgata
aaattacggcggcaacacaagagttcgaggcgaggcagcagcggccaaca
gcatccgtaactgcgctgtctagagacccgaattggatcaattcatggt
aaattaattatcaaactgaattatagtgggtcgtttcttcaagtgtatat -continued gttaagtctttattttgtttgtatcgtaaattttatcaacaggaagcat
actgtgatatgctggttaaatatcgagaggagctaacacggcccattgaa
gaagcaatggagtatatacgtcgtattgaatctcagattagcatgttgtg
tcagtcccattcacatcctcaacaatcctggtaaatgtcataaaactcac
aaatacatatacatgcatatacccacatgtaaccattgaatgtagaaaag
aaaatataatgccaaggtagggctcatgatgaatttcaagagcaacattg
gcgcgtatttctttggttcccgggaaagttttgtaccaattagattatga
taaggcgaccaaaaaataattatgattatatttggttaaaattttcatc
taaacattcaagtgttaattaagatcataaaatataatagttaatatgat
agaaattcgtaggctgcagacagatgtgcacatttgctcttgttttccct
attgtagaatccatccaaagagggtggggcttttttggtttcttacttt
taacccggcccaaagtactactgtcacaaacacttttttgttgttcactat
gaaaaaaatacaaataggtattctcaattccagtatgcaaaatgtttca
aattttcataaaaaagtcagtacgactaaattgctcgtgaattatgaatc
aaaatataagactgatgaaaagctaaaatttgaaacagatgggaaaagtg
aaggaatggaatcatcagacgaagagcaagataataacaacagtggaggg
gaagcagaaattaccggaaatagacccggagggcggaagatcgggaactc
aagaatcacttgctgaagaagtacagtggatacttgagcagtctaaagca
agaactgtccaagaaaaaaagaaaggtaaacttcccaaagaagcaaggc
agaagcttctcacgtggtgggaattgcattacaagtggccgtatccttct
gtacgtataattttactctcatctctctatgctttcagtcttttaaaata
tacactctatataaatactagaaccagtctttggaaaacaatgtagatg
ctgggaatctccaatttgccctgattttctctaaagggccttccttaggc
cgattaggctctttgcagggatcatttgtagatgctaggctctttgcaga
gataatttgtgttcaaaccttatgcgtttccatatttcataacatatgt
atatacatatatcaaacacgtttttatctatagttatctaaattttga
aataattttgaagtttaagtccgtggatctattgttatagtttatcagct
tcaggaaataaaacaaataaaaccgaatgtggtgatggcgaaggtcttta
atattgggatacatatttaccacaaaaaaaatgatatattatatagaat
ggctgtttgttgttaaaaaatcctggtatttttttggtaaatatgatac
cattccaatgaacaccaaaaatgataccatcccaccaaatttgttgtaa
tgtaaaaagtattacaccaaattaacaatattcattacaccaaatattaa
aataatatttattattttttatttaataatagatagattagtttttt
acttagttataacttatagttaaaatgagtatatcataatatcttgtatt
tttaatccatattttacattactaaaacattaaactattattttatttt
ataatttaattaatagtatataattaaatgagtattataaattatattaa
atggtaacaaaataaaaatgatcttcattttaaatgcaaaagttttaat
ttttacaaatattttaaataaaataataataaagtatacacattmacta
aagaaaaatagcttatataaaaataaaattaccaaatatttaatatatat
atatatatatatataaactaaatgtgatacatatatataattagtcaatt -continued ataaacaattatgtattaaattactaaaactaaaaagttgataatataaa
atattattttggtgtagaatttggtgtgatggttggacatgaaaaataaa
gtttaacmcttaaacmccmmtyctggtgtaatttcarcactaattttagt
gttatggttggagataccctaacagaaccatgcttcgtgctttgaaaaaa
aaatcagtcgtctaaagctacaataaaaaaattggagggaaatattttgt
ttcaaattaggttatgtatttacacagatatttgtttggattcttgtctg
agaagtgcatggcattacattttgtgttacaaaagaagttgaatgatctg
agtatcatatttattgaaagcgtgttggtatatgtgtgttgctaaaaagt
tctataagaaaattggataaatttgctttaaaatttccatagtatatcac
tattttgtatgttcggaaaccttgatatgtatactttccccttataacga
gggccttaatattctttagtcatctagattgttcgaagcagcagactgta
atttataacttcgtctgactatcatctacctttttttatagaacatacctt
ttcttttattgaaactaatcgtctagcttttgtgattaaatctaccgt
ttttaaacaatgaacaatactaaaaaagtgatgatatggatatggttctg
atttgtgttgtgtggcaggagtcagagaaggtggcgttggcggaatccaa
cggggttagatcagaaacagatcaacaattggttcataaaccaaagaaaa
cgtcactggaaaccgccgaagacatgcagttcatggtgatggatggtcta
cagcacccgcaccacgcagctctatacatggatggtcattacatgggcga
tggtcctatcgtcttggaccataagagaccgcatgcagatatccagaag
ggttagccatataataacaaccttttgttgcctctctcgtttacagttca
tgatttcaacttccttcacaagtttgctacctatagcttttattttctta
cccgtatttaatgtcttatatcgttcaagggggtttgagacttcctagt3'

SEQ ID NO: 21: PCR Primer (Synthetic DNA)
5'-catgatcggatcggaagcaattctcagtcg-3'

SEQ ID NO: 22: PCR Primer (Synthetic DNA)
5'-aaaagttgagagagaaagagagagagagag-3'

SEQ ID NO: 23:
BnBP promoter (Bnbppr900) (Genomic DNA)
5'aaaaaaatgcttacaaatatctgcacatcaaccaatctgttacataaat
agatcttcttgtgggggtagggttaacaaatattttcctcttttttctttt
ctcaaaaatgtatcggtactgatatagccgcggagacctggttcattaaa
acattggcggtacatcttaataatcaaaacattgacggcacatcttaatc
ctagagtttaaccacattatatatcatagagtaacaaacttagttttga
cccaaaagaagaaaaaaacttccaattttctagtacagaataagcctac
gagagggaaacagaagagaaaggaggaaagaagggaagcctttgccttat
ctcttgtccattctctcttaccttttattttaattttcaaatatttatta
ttgccaccaaagcaaacgacgtcttgtcaatccactcaacccacccaact
tcttaattattgttaacacatctctcctctttctctctcatctttttata
atttcttctcttccatgtcacttttttgacgaattctatttacttagttcg
ttttttcttcctcaaaatatctcgttttcaatttatttgttttgttgggt
gcaacttcacctcacaattttttttatgaagcacctttctgattcgtaga
tatgagtcgtctagtcatgggatttgatttggttaaagtctaacatcgac
ctttgattgaaataaggacaaaagaaagaatacatacatcccccttcattt
tgcacccatcccctttattttctaggggtttattttttatcacattagttttt
ttatattctctctctctctctctctttctctctcaactttt3'

SEQ ID NO: 24:
BnBP promoter (Bnbppr 1000) (Genomic DNA)
5'aaatctttatcttctctgtttcttgtgcaatcttctatccgaaaacga
gtacaatataatctctctccaccgatgtaatacgaatatcaaatcagaaa
ttaatcatttgatcatattctcaaaacatctaaatttattttacaaattg
cttacaaatatctgcacatcaaccaatctgttacataaatagatcttctt
gtaggggtaaggttaacaaatattttttcttttttcttttctccaaaatg
tatcggtactgatatagccgcggagacctggttcatcaaaacattgacgg
tacatcttaattcgagagtttaaccaaattatatcatagagtaacaaact
tagtttttgacccaaaataagagaaaaaactttcaattttctaatacgga
ataagctatgagagggagacagaagagaaagtaggaaagaagggaagcct
ttgccttatctcttgtccattctctcttacctttatttaattttcaaat
atttattattgccaccaaagcaaacgacgtcttgtcaatccactcaaccc
acccaacttcttaattattgttaacacatctctcctctttctctctcatc
tttttataatttcttctcttccatgtcacttttttgacgaattctatttac
ttagttcgttttttcttcctcaaaatatctcgttttcaatttatttgttt
tgttgggtgcaacttcacctcacaattttttttatgaagcacctttctga
ttcgtagatatgagtcgtctagtcatgtggatttgatttggttaaagtct
aacatcgacctttgattgaaataagaacaaaagaaagaatacatacatcc
ccttcattttgcacccatcccctttattttctagggtttatttttatcac
attagttttttatattctctctctctctctctcttctctctcaactttt
t3'

The invention claimed is:

1. A method of producing a transgenic plant comprising the steps of:
  (a) introducing into a plant cell capable of being transformed and regenerated into a whole plant a construct comprising, in addition to the DNA sequences required for transformation and selection in plants, the nucleotide sequence as set forth in SEQ ID No. 20 operably linked to a promoter in sense orientation, wherein expression of said nucleotide sequence increases the expression of the plant's native *brevipedicellus* gene; and
  (b) recovery of a plant which contains said nucleotide sequence and has increased pedicel length compared to an unmodified plant.

2. The method according to claim 1, characterised in that said plant is of the genus *Arabidopsis*.

3. The method according to claim 1, characterised in that said plant is of the genus *Brassica*.

4. The method according to claim 1, characterised in that said plant is selected from the group consisting of: a dicot, a monocot, and a member of Cruciferae.

5. The method according to claim 1, characterised in that said promoter comprises a transcriptional regulatory region normally in operable association with an endogenous *brevipedicellus* gene or homologue thereof.

6. The method according to claim 1, characterised in that said promoter comprises a transcriptional regulatory region that is not normally in operable association with an endogenous *brevipedicellus* gene or homologue thereof.

7. The method according to claim 1, characterised in that said promoter is selected from the group consisting of: a constitutive promoter, an inducible promoter, an organ specific promoter, a strong promoter, a weak promoter, and an endogenous promoter from *Arabidopsis* as set forth in SEQ ID No. 24.

8. A method of identifying a plant that has been successfully transformed with a construct, characterised in that the method comprises the steps of:

(a) introducing into plant cells capable of being transformed and regenerated into whole plants a construct comprising, in addition to the DNA sequences required for transformation and selection in plants, the nucleotide sequence as set forth in SEQ ID No. 20, operably linked to a promoter in sense orientation, wherein expression of said nucleotide sequence increases the expression of the plant's native *brevipedicellus* gene;

(b) regenerating said plant cells into whole plants; and (c) inspecting said plants for increased pedicel length compared to the plants before introduction of said nucleotide sequence to determine those plants successfully transformed with said construct, and expressing said nucleotide sequence.

9. The method according to claim 8, characterised in that said plant cells and said regenerated whole plants harbour a *brevipedicellus* mutation, and successful transformation and expression of said nucleotide sequence complements said mutation, thereby generating a plant exhibiting wild-type phenotype.

10. The method according to claim 9, characterised in that said construct is bicistronic and further comprises a second DNA expression cassette for generating a transcript unrelated to said nucleotide sequence.

11. A transgenic plant generated by the method according to claim 1.

12. The transgenic plant according to claim 11, characterised in that said transgenic plant is of the genus *Arabidopsis*.

13. The transgenic plant according to claim 11, characterised in that said transgenic plant is of the genus *Brassica*.

14. The transgenic plant according to claim 11, characterised in that said plant is selected from the group consisting of: a dicot, a monocot, and a member of Cruciferae.

15. An isolated nucleotide sequence for generating a transgenic plant with increased pedicel length compared with an unmodified plant, characterised in that said isolated nucleotide sequence is as set forth in SEQ ID No. 20.

* * * * *